(12) United States Patent
Giacosa et al.

(10) Patent No.: US 10,322,133 B2
(45) Date of Patent: Jun. 18, 2019

(54) SYNTHETIC LETHAL DRUG COMBINATION FOR TREATING RENAL CELL CARCINOMA

(71) Applicants: Commissariat a l'Energie Atomique et aux Energies Alternatives, Paris (FR); Institut National de la Sante et de la Recherche Medicale (INSERM), Paris (FR)

(72) Inventors: Sofia Giacosa, La Tour du Pin (FR); Catherine Pillet, Vif (FR); Claude Cochet, Claix (FR); Odile Filhol, Claix (FR); Caroline Barette, Sassenage (FR); Emmanuelle Soleilhac, Saint Etienne de Crossy (FR)

(73) Assignees: Commissariat a l'Energie Atomique et aux Energies Alternatives, Paris (FR); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 15/759,815

(22) PCT Filed: Sep. 21, 2016

(86) PCT No.: PCT/EP2016/072458
§ 371 (c)(1),
(2) Date: Mar. 13, 2018

(87) PCT Pub. No.: WO2017/050842
PCT Pub. Date: Mar. 30, 2017

(65) Prior Publication Data
US 2018/0256587 A1 Sep. 13, 2018

(30) Foreign Application Priority Data
Sep. 21, 2015 (EP) .................... 15306469

(51) Int. Cl.
| | |
|---|---|
| A61K 45/06 | (2006.01) |
| A61P 35/00 | (2006.01) |
| A61K 31/437 | (2006.01) |
| A61K 31/4375 | (2006.01) |
| A61K 31/4745 | (2006.01) |
| A61K 31/5377 | (2006.01) |

(52) U.S. Cl.
CPC ........ *A61K 31/5377* (2013.01); *A61K 31/437* (2013.01); *A61K 31/4375* (2013.01); *A61K 31/4745* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | |
|---|---|---|
| 2009/0054507 A1 | 2/2009 | Kalafatis |
| 2009/0099191 A1 | 4/2009 | Gudkov |

FOREIGN PATENT DOCUMENTS

| | | |
|---|---|---|
| WO | 2009/032213 A1 | 3/2009 |
| WO | 2011/133668 A2 | 10/2011 |

OTHER PUBLICATIONS

International Search Report issued in corresponding International Patent Application No. PCT/EP2016/072458 dated Jan. 16, 2017.
Written Opinion issued in corresponding International Patent Application No. PCT/EP2016/072458 dated Jan. 16, 2017.
Arteaga et al., "Elliptinium, a DNA intercalating agent with broad antitumor activity in a human tumor cloning system," European Journal of Cancer and Clinical Oncology, 23: 1621-1626 (1987).
Siddiqui-Jain et al., "CX-4945, an Orally Bioavailable Selective Inhibitor of Protein Kinase CK2, Inhibits Prosurvival and Angiogenic Signaling and Exhibits Antitumor Efficacy," Cancer Research, 70: 10288-10298 (2010).
Garner et al., "Inhibition of ATM sensitizes cells to the topoisomerase I inhibitor SN38," American Association for Cancer Research, 50: 1109-1110 (2009) (abstract only).
Prudent et al., "Antitumor Activity of Pyridocarbazole and Benzopyridoindole Derivatives that Inhibit Protein Kinase CK2," Cancer Research, 70: 9865-9874 (2010).

*Primary Examiner* — Brian J Davis
(74) *Attorney, Agent, or Firm* — Morgan, Lewis & Bockius LLP

(57) ABSTRACT

The present invention pertains to a novel treatment of renal cell carcinoma and other a solid tumors which harbor a VHL inactivation, based on the combination of a first agent inhibiting a protein kinase CK2 (CK2) and a second agent inhibiting an Ataxia Telangiectasia Mutated (ATM) kinase.

15 Claims, 17 Drawing Sheets
Specification includes a Sequence Listing.

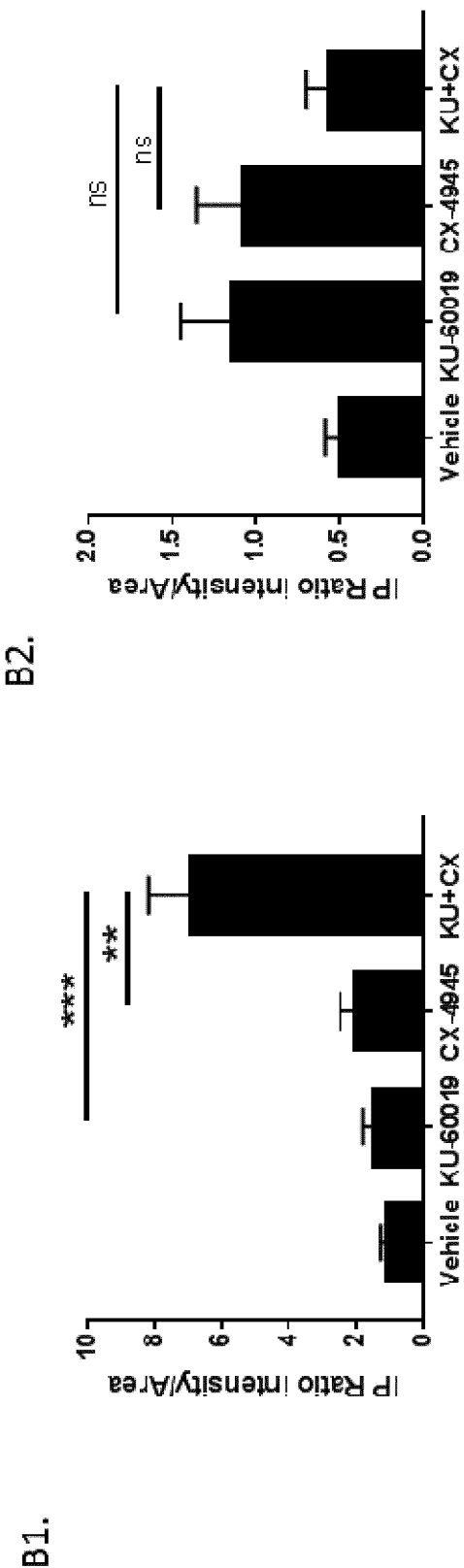
Figures 10B1 and 10B2

SYNTHETIC LETHAL DRUG COMBINATION FOR TREATING RENAL CELL CARCINOMA

SEQUENCE LISTING SUBMISSION VIA EFS-WEB

A computer readable text file, entitled "SequenceListing.txt," created on or about Mar. 8, 2018 with a file size of about 11 kb contains the sequence listing for this application and is hereby incorporated by reference in its entirety.

The present invention pertains to the domain of cancer treatment. More precisely, the present invention relates to a novel combined treatment of renal cell carcinoma.

Renal cell carcinoma (RCC) is the eighth leading malignancy in the world, accounting for 4% of all cancers. Approximately 30% of RCC patients present with metastatic disease at the time of diagnosis and nearly half of the remainder will subsequently develop metastasis (mRCC) (Negrier, Escudier et al. 1998, McDermott, Regan et al. 2005).

Clear Cell Renal Cell Carcinoma (ccRCCs) is the most common form of kidney cancer, accounting for 75% of all cases (Lopez-Beltran, Scarpelli et al. 2006).

Inactivating or silencing mutations of the Von Hippel Lindau (VHL) Tumor Suppressor Gene represents ccRCC fingerprints.

It has been shown that, under normoxic conditions, the oxygen-sensitive HIFα subunit is degraded by VHL-mediated ubiquitination. However, under hypoxic conditions, HIFα degradation is suppressed, leading to enhanced nuclear localization of HIFα and transcription of various target genes, including the angiogenic factor gene VEGF (Kaelin 2008) and other genes involved in tumor progression and metastasis.

RCC is notably highly resistant to chemotherapy. Moreover, treatment of mRCC is difficult because it shows no or limited responsiveness to conventional anticancer therapies, such as radiation, chemotherapy and cytokine therapy (Figlin, Sternberg et al. 2012).

However, several available kinase-targeted agents have shown beneficial effects for the treatment of patients with metastatic renal cell carcinoma (mRCC), including Tyrosine Kinase inhibitors (TKIs) like sunitinib, sorafenib, pazopanib and axitinib, the VEGF-targeted antibody bevacizumab and the mammalian target of rapamycin (mTOR) inhibitors temsirolimus and everolimus (Maj-Hes, Medioni et al. 2013). Although these targeted agents demonstrate antitumor activity and prolonged progression-free survival (PFS) some patients treated with them experience disease progression.

Thus, the lack of long-term efficacy of current treatments reveals the urgent need to find other therapies focusing on the different pathways involved in this devastating disease.

To this aim, the inventors have taken advantage of a new approach called "synthetic lethality". In classical genetics, this term refers to the interaction between two genetic perturbations which confer lethality when combined, whereas each perturbation alone does not. Synthetic lethality can also apply to cases in which the combination of a mutation or inactivation of one gene and the action of a chemical compound causes lethality, whereas the mutation/inactivation or the compound alone is non-lethal. A synthetic lethal approach to cancer therapy is currently being explored as a means to develop targeted therapies to reduce off-target effects in chemotherapies and chemopreventive drugs (McLornan, List et al. 2014).

Genetic or pharmacological interference are among major mechanisms to achieve synthetic lethality in cancer. New drug combinations can be identified from high-throughput screening using small interfering RNA (siRNA), short hairpin RNA (shRNA) and/or small chemical inhibitors.

To achieve this, the inventors have performed a novel type of screening. As described in the experimental part below, they used the highly aggressive 786-O VHL null ccRCC human cell line and combined 36 shRNAs to silence different genes that have been shown to be involved in different types of cancer with 80 different drugs (FDA and non-FDA approved). By doing so, they identified several gene-drug interactions including synthetic-lethal interactions between components of signaling pathways and specific kinase inhibitors. Among them, the shRNA-mediated knockdown of CK2α expression enhanced the sensitivity of 786-O VHL⁻ cells to KU-60019 (Selleckchem), an inhibitor of Ataxia Telangiectasia Mutated (ATM) kinase. The same effect was also observed when the cells were treated with a combination of KU-60019 and CX-4945, a protein kinase CK2 inhibitor. Moreover, this synergistic anti-proliferative effect of the combination was much stronger in 786-O VHL⁻ cells as compared to 786-O VHL⁺ cells. This differential effect was also observed with the RCC4 VHL⁻ and RCC4 VHL⁺ cell lines, indicating that simultaneous pharmacologic inhibition of ATM and CK2 acted in a synergistic fashion to specifically impede VHL null ccRCC cell growth in a manner greater than the individual inhibitors alone.

The role of CK2 (formerly called "casein kinase II"), and ATM kinases in cell survival signaling pathways and their implication in cancer are well documented in the literature.

CX-4945 has been shown to be effective in several in vitro and preclinical studies (Siddiqui-Jain et al., *Cancer Res* Dec. 15, 2010 70; 10288). The results show that CX-4945 can induce stabilization of the disease in several types of cancer. CX-4945 has been tested in Phase I of clinical trials in several types of solid tumors including Renal Carcinoma (Marschke et al., *Mol Cancer Ther* 2009; 8(12 Suppl): C39).

ATM inhibitor KU-60019 was used to radiosensitize gliomas cells (Golding et al, 2009), and was also tested in preclinical studies (Vechio et al., 2014).

Despite the fact that both kinases have been considered as relevant targets for the development of pharmacological inhibitors, the results disclosed below constitute the first demonstration that dual targeting of CK2 and ATM leads to a synergistic inhibition of proliferation/survival of cancer cells.

The present invention hence pertains to a combination of a first agent inhibiting a protein kinase CK2 (CK2) and a second agent inhibiting an Ataxia Telangiectasia Mutated (ATM) kinase, for use as a medicament.

In what precedes, the "first agent inhibiting a CK2" can be any molecule inhibiting either the expression or the activity of said CK2. In particular, the first agent can be a chemical molecule inhibiting the kinase activity of CK2, a siRNA targeting a gene encoding CK2α and/or α' (thereby inhibiting its expression) or a shRNA targeting a gene encoding CK2α and/or α' (thereby inhibiting its expression). Similarly, the "second agent inhibiting an ATM kinase" can be any molecule inhibiting either the expression or the activity of said ATM kinase. Examples of such agents are chemical molecules inhibiting the kinase activity of ATM kinase, siRNAs targeting a gene encoding ATM kinase and shRNAs targeting a gene encoding ATM kinase.

According to a particular embodiment, first agent inhibiting a protein kinase CK2 (CK2) is as described in WO 2005/005632, that is to say double-stranded oligonucleotides made up of two strands of 19 to 23 nucleotides, each strand consisting, from 5' to 3', of a sequence of 17 to 21 ribonucleotides and two deoxyribo- or ribonucleotides, the 17 to 21 ribonucleotide RNA sequences of said strands being complementary and the two nucleotides of the 3' ends being protruding, characterized in that the RNA sequence of the sense strand or positive strand is that of a fragment of a transcript of an α, α' or β subunit of a CK2 protein kinase, selected from the group consisting of:

a) a fragment corresponding to an oligonucleotide which inhibits more than 80% of the expression of the corresponding subunit, in cell culture, at a concentration of between 1 and 200 nM, preferably less than 20 nM, b) a fragment of a transcript of an α subunit included between positions 18-74, 259-279, 565-585, 644-664, 720-750, 808-831 and 863-885, from the ATG codon, with reference to the cDNA sequence of the CK2 α subunit of mouse No. NM 007787 or human No. NM 001895, c) a fragment of a transcript of an α' subunit included between positions 49-69, 132-142, 306-326, 367-387, 427-447, 451-471, 595-615, 735-755, 827-847, 868-888, 949-969 and 988-1008, from the ATG codon, with reference to the cDNA sequence of the CK2 α' subunit of mouse NM 009974 or human No. NM 001896, and d) a fragment of a transcript of a β subunit included between positions 80-100, 116-127, 164-208, 369-389, 400-420, 527-591 and 613-643, from the ATG codon, with reference to the cDNA sequence of the CK2 β subunit of human No. NM 001320 or of mouse No. NP 034105, and e) a fragment of 17 to 21 nucleotides exhibiting at least 80% identity with the fragments defined in a), b), c) and d).

The double-stranded oligonucleotide corresponds to an siRNA capable of inhibiting the expression of the corresponding subunit of the CK2 protein kinase; the 17 to 21 nucleotide RNA sequence of the sense strand or positive strand is that of the target sequence of the transcript of the α, α' or β subunit of the mammalian CK2 protein kinase.

The invention encompasses the natural, synthetic, semi-synthetic or recombinant oligonucleotides targeting the CK2 protein kinase of any organism, in particular eukaryotic organism. Given the information provided with reference to the human and mouse sequences, those skilled in the art are in a position to find the equivalent positions in the sequences of other eukaryotic organisms, in particular of mammals, that are accessible in the sequence data bases.

In accordance with the invention, the identity of an oligonucleotide sequence with respect to a reference sequence is assessed as a function of the percentage of nucleotides that are identical, when the sequences are aligned, so as to obtain the maximum correspondence between them.

According to an advantageous embodiment of said double-stranded oligonucleotide, said sequence is selected from the group consisting of:

a) a fragment of an α subunit defined by the RNA equivalent of the sequence SEQ ID Nos: 1 to 13, b) a fragment of an α' subunit defined by the RNA equivalent of the sequence SEQ ID Nos: 14 to 25, c) a fragment of a β subunit defined by the RNA equivalent of the sequence SEQ ID Nos: 26 to 40, and d) a sequence as defined in a), b) or c), truncated by one or two nucleotides at its 5' and/or 3' end.

For the purpose of the present invention, the expression "RNA equivalent of a DNA sequence" is intended to mean the sequence in which the deoxyribonucleotides (a, g, c, t) of said DNA sequence are replaced with the ribonucleotides (a, g, c, u).

According to another advantageous embodiment of said double-stranded oligonucleotide, each of the strands comprises a phosphate group in the 5' position and a hydroxyl group in the 3' position.

According to yet another advantageous embodiment of said double-stranded oligonucleotide, said protruding nucleotides of the 3' ends are selected from the group consisting of the pairs tt and aa.

According to yet another advantageous embodiment of said double-stranded oligonucleotide, it is made up of two strands of 19 or 20 nucleotides.

According to an advantageous arrangement of this embodiment of said double-stranded oligonucleotide, it comprises a sense strand defined by the sequence SEQ ID No. 67 or 68.

According to yet another advantageous embodiment of said double-stranded oligonucleotide, it is made up of two stands of 21 to 23 nucleotides.

According to an advantageous arrangement of this embodiment of said double-stranded oligonucleotide, it comprises a sense strand as defined by the sequence SEQ ID Nos. 41 to 66, 69 to 81, 83 and 86.

Tables I, II and III below summarize the properties of the various oligonucleotides of sequences SEQ ID Nos. 1 to 86.

TABLE I target sequences and SiRNA α

| Name and No. | Mouse target sequence (sense sequence) | SiRNA | Size | Tm | % GC | Position/ATG codon NM_007787 mouse and NM_001895 of the human sequence | Hu*/mouse homology |
|---|---|---|---|---|---|---|---|
| CK2α1 | cagaccccgagagtactggga (SEQ ID NO: 3) | gaccccgagaguacugggatt ttcuggggcucucaugacccu (SEQ ID NO: 44) | 21 | 61.5 | 57 | 54 | 2 |
| CK2α2 | aacacacacagaccccgagag (SEQ ID NO: 2) | aauacacacagaccucgagtt ttuuaugugugucuggagcuc (SEQ ID NO: 43) | 21 | 61.7 | 52.4 | 46 | 2 |
| CK2α3 | aagcagggccagagtttacac (SEQ ID NO: 1) | gcagggccagaguuuacactt ttcgucccggucucaaaugug (SEQ ID NO: 41) | 21 | 58.6 | 52.4 | 18 | 0 |

TABLE I-continued target sequences and SiRNA α

| Name and No. | Mouse target sequence (sense sequence) | SiRNA | Size | Tm | % GC | Position/ATG codon NM_007787 mouse and NM_001895 of the human sequence | Hu*/mouse homology |
|---|---|---|---|---|---|---|---|
| CK2α4 | aacacacacagaccccgagag (SEQ ID NO: 2) | cacacacagaccccgagaguu ttgugugugucuggggcucuc (SEQ ID NO: 42) | 21 | 59.3 | 52.4 | 46 | 2 |
| CK2α5 | aatttgagaggtgggcccaac (SEQ ID NO: 4) | uuugagaggugggcccaacuu ttaaacucuccacccggguug (SEQ ID NO: 45) | 21 | 59.8 | 52.4 | 259 | 2 |
| CK2α6 | aatgtccgagttgcttctcga (SEQ ID NO: 5) | uguccgaguugcuucucgauu ttacaggcucaacgaagagcu (SEQ ID NO: 46) | 21 | 58.8 | 47.6 | 565 | 1 |
| CK2α7 | aacgatatcttgggcagacac (SEQ ID NO: 10) | cgauaucuugggcagacacuu ttgcuauagaacccgucugug (SEQ ID NO: 51) | 21 | 57.9 | 47.6 | 808 | 1 |
| CK2α8 | aaaaccagcatcttgtcagcc (SEQ ID NO: 12) | aaccagcaccuugucagccuu ttuuggucguggaacgaucgg (SEQ ID NO: 53) | 21 | 60.3 | 47.6 | 863 | 2 |
| CK2α9 | aaccagcatcttgtcagccct (SEQ ID NO: 13) | ccagcaccuugucagcccuuu ttggucguggaacagucggga (SEQ ID NO: 54) | 21 | 62.0 | 52.4 | 865 | 2 |
| CK2α10 | aggatagccaaggttctgg (SEQ ID NO: 9) | aggauagccaagguucugguu ttuccuaucgguuccugacc (SEQ ID NO: 50) | 21 | 58.9 | 47.6 | 730 | 0 |
| CK2α11 | tggtgaggatagccaaggttc (SEQ ID NO: 8) | gugaggauagccaagguucuu ttcacuccuaucgguuccaag (SEQ ID NO: 49) | 21 | 57.1 | 47.6 | 725 | 0 |
| CK2α12 | tcagttggtgaggatagcca (SEQ ID NO: 7) | caguuggugaggauagccauu ttgucaaccacuccuaucggu (SEQ ID NO: 48) | 21 | 58.8 | 47.6 | 720 | 0 |
| CK2α13 | gatatcttgggcagacactcc (SEQ ID NO: 11) | uaucuugggcagacacuccuu ttauagaacccgucugugagg (SEQ ID NO: 52) | 21 | 58.6 | 47.6 | 811 | 1 |
| CK2α14 | tgtggagcttgggttgtatgc (SEQ ID NO: 6) | uggagcuuggguuguaugcuu ttaccucgaacccaacauacg (SEQ ID NO: 47) | 21 | 61.8 | 47.8 | 644 | 1 |

*Hu = human
NB: the ATG is at position 1 of the mouse sequence No. NM 007787 and in position 277 of the human sequence No. NM 001895.

TABLE II target sequences and SiRNA α'

| Name | Human target sequence (sense sequence) | SiRNA | SIZE | Tm | % GC | Position | Hu/mouse homology |
|---|---|---|---|---|---|---|---|
| CK2α'1 | aacagtctgaggagccgcgag (SEQ ID NO: 14) | cagccugaggagccgcgaguu ttgucggacucccggcgcuc (SEQ ID NO: 55) | 21 | 66.5 | 66.7 | 49 | 1 mismatch |
| CK2α'2 | aaaacttggtcggggcaagta (SEQ ID NO: 15) | aacuuggucggggcaaguauu ttuugaaccagccccguucau (SEQ ID NO: 56) | 21 | 59.5 | 47.6 | 132 | 2 mismatches |
| CK2α'3 | aaaggaccctgtgtcaaagac (SEQ ID NO: 16) | aggacccugugucaaagacuu ttccugggacacaguuucug (SEQ ID NO: 57) | 21 | 62.4 | 47.6 | 306 | 1 |

TABLE II-continued target sequences and SiRNA α'

| Name | Human target sequence (sense sequence) | SiRNA | SIZE | Tm | % GC | Position | Hu/mouse homology |
|---|---|---|---|---|---|---|---|
| CK2α'4 | aagcaactctaccagatcctg (SEQ ID NO: 17) | gcaacucuaccagauccuguu ttcguugagauggucuaggac (SEQ ID NO: 58) | 21 | 55.8 | 47.6 | 367 | 0 |
| CK2α'5 | aaagctctggattactgccac (SEQ ID NO: 18) | agcucuggauuacugccacuu ttucgagaccuaaugacggug (SEQ ID NO: 59) | 21 | 58.2 | 47.6 | 427 | 0 |
| CK2α'6 | aagggaatcatgcacagggat (SEQ ID NO: 19) | gggaaucaugcacagggauuu ttcccuuaguacgugucccua (SEQ ID NO: 60) | 21 | 62.8 | 47.6 | 451 | 0 |
| CK2α'7 | aagggaccagagctccttgtg (SEQ ID NO: 20) | gggaccagagcuccuugguu ttcccuggucucgaggaacuc (SEQ ID NO: 61) | 21 | 65.2 | 57.1 | 595 | 1 |
| CK2α'8 | aattgccaaggttctgggac (SEQ ID NO: 21) | uugccaagguucuggggacuu ttaacgguuccaagaccccug (SEQ ID NO: 62) | 21 | 61.5 | 52.4 | 735 | 2 but at the ends |
| CK2α'9 | aacattcacggaagcgctggg (SEQ ID NO: 22) | cauucacggaagcgcugggu ttguaagugccuucgcgaccc (SEQ ID NO: 63) | 21 | 66.4 | 57.1 | 827 | 1 |
| CK2α'10 | aacaggccaccttgtcagcccg (SEQ ID NO: 23) | caggcaccuugucagcccguu ttguccgguggaacagucgggc (SEQ ID NO: 64) | 21 | 61.0 | 61.9 | 868 | 20 of which one is the last nt |
| CK2α'11 | aaagaggccatggagcaccca (SEQ ID NO: 24) | agaggccauggagcacccauu ttucuccgguaccucguggu (SEQ ID NO: 65) | 21 | 68.4 | 57.1 | 949 | 0 |
| CK2α'12 | aaggagcagtcccagccttgt (SEQ ID NO: 25) | ggagcaguccccagccuuguu ttccucgucaggggucggaaca (SEQ ID NO: 66) | 21 | 64.6 | 57.1 | 988 | 0 |

NB: The ATG is at position 99 of the mouse sequence No. NM 009974 and at position 164 of the human sequence No. NM 001896.

TABLE III target sequences and SiRNA β

| Name | Human target sequence (No) | SiRNA | Size | Tm | % GC | Position | Hu/mouse homology |
|---|---|---|---|---|---|---|---|
| CK2β1 | aagacaaccccaaccagagtg (SEQ ID NO: 32) | aagacaaccccaaccagagug ccuucguuggguuggucuc (SEQ ID NO: 73) | 21 | 61.2 | 52.4 | 188 | 0 mismatch |
| CK2β2 | tcaatgagcaggtccctcact (SEQ ID NO: 27) | aaugagcaggucccucacu aguuacucguccagggagu (SEQ ID NO: 68) | 21 | 62 | 52.4 | 116 | 0 |
| CK2β3 | acctggagcctgatgaagaac (SEQ ID NO: 29) | accuggagccugaugaagaac ccuggaccucggacuacuucu (SEQ ID NO: 70) | 21 | 60.5 | 52.4 | 164 | 1 |
| CK2β4 | tggagcctgatgaagaactgg (SEQ ID NO: 30) | uggagccugaugaagaacugg ggaccucggacuacuucuuga (SEQ ID NO: 71) | 21 | 62.5 | 52.3 | 167 | 1 |
| CK2β5 | ggagcctgatgaagaactgga (SEQ ID NO: 31) | ggagccugaugaagaacugga gaccucggacuacuucuugac (SEQ ID NO: 72) | 21 | 62.5 | 52.3 | 168 | 1 |
| CK2β6 | caatgagcaggtccctcacta (SEQ ID NO: 28) | caaugagcagguccccucacua gaguuacucguccagggagug (SEQ ID NO: 69) | 21 | 60.1 | 52.3 | 117* | 0 |
| CK2β7 | ccaagagacctgccaaccagt (SEQ ID NO: 35) | ccaagagaccugccaaccagu cgguucucuggacgguugu (SEQ ID NO: 76) | 21 | 62 | 47.6 | 527 | 1 |

TABLE III-continued target sequences and SiRNA β

| Name | Human target sequence (No) | SiRNA | Size | Tm | % GC | Position | Hu/mouse homology |
|---|---|---|---|---|---|---|---|
| CK2β8 | cctgtcggacatcccaggtga (SEQ ID NO: 33) | ccugucggacaucccagguga ccggacagccuguaggucca (SEQ ID NO: 74) | 21 | 62.2 | 52.3 | 369 | 3 |
| CK2β9 | agcaacttcaagagcccagtc (SEQ ID NO: 38) | agcaacuucaagagcccaguc ggucguugaaguucucgdguc (SEQ ID NO: 79) | 21 | 60.8 | 52.3 | 613 | 0 |
| CK2β10 | ccaggctctacggtttcaaga (SEQ ID NO: 36) | ccaggcucuacgguuucaaga cggguccgagaugccaaaguu (SEQ ID NO: 77) | 21 | 60.5 | 52.3 | 554 | 1 |
| CK2β11 | agagcccagtcaagacgattc (SEQ ID NO: 40) | agagcccagucaagacgauuc guucucggdgucaguucugcua (SEQ ID NO: 81) | 21 | 60.6 | 52.3 | 623 | 0 |
| CK2β12 | aacttcaagagcccagtcaag (SEQ ID NO: 39) | aacuucaagagcccagucaag gcuugaaguucucgggucagu (SEQ ID NO: 80) | 21 | 60.8 | 52.3 | 616 | 0 |
| CK2β13 | aagctctactgccccaagtgc (SEQ ID NO: 34) | gcucuacugccccaagugcuu ucgagaugacgggguucacg (SEQ ID NO: 75) | 21 | 63 | 52.4 | 400 | 1 |
| CK2β14 | aagatccatccgatggcctac (SEQ ID NO: 37) | gauccauccgauggccuacuu uucuagguaggcuaccggaug (SEQ ID NO: 78) | 21 | 62.3 | 42.9 | 571 | 2 |
| CK2β15 | aagactacatccaggacaat (SEQ ID NO: 26) | gacuacauccaggacaauuu ucugauguaggucuguua (SEQ ID NO: 67) | 21 | 52.1 | 38.1 | 80 | 0 |
| CK2β16 | aagactacatccaggacaat (SEQ ID NO: 26) | aagacuacauccaggacaauu uuucugauguagguccuguu (SEQ ID NO: 83) | 21 | | | | |
| CK2β17 | aagactacatccaggacaat (SEQ ID NO: 26) | ugaagacuacauccaggacuu uuacuucugauguagguccug (SEQ ID NO: 86) | 21 | | | | |

NB: The ATG is in position 341 of the human sequence No. NM 001320.

The first agent inhibiting a protein kinase CK2 (CK2) is also a single-stranded oligonucleotide, characterized in that it is defined by the antisense strand or negative strand of the double-stranded oligonucleotide as defined above.

According to an advantageous embodiment of the double-stranded or single-stranded oligonucleotide as defined above, it is stabilized.

Stabilized oligonucleotides are known to those skilled in the art; they can be stabilized in particular by incorporation of modified bases during the in vitro synthesis or by modifications of the bases incorporated beforehand into said oligonucleotides. Examples of these modifications are given in Table IV below.

TABLE IV

| Modified nucleotide | First application | Second application |
|---|---|---|
| 2′ F-CTP | Resistance to nuclease | |
| 2′F-UTP | Resistance to nuclease | |
| 2′NH2-CTP | Resistance to nuclease | |
| 2′NH2-UTP | Resistance to nuclease | |
| 2′N3-CTP | Resistance to nuclease | Post-synthesis modification |
| 2′N3-UTP | Resistance to nuclease | Post-synthesis modification |
| 2-thio CTP | UV-crosslinking | |
| 2-thio UTP | Modified hybridization | UV-crosslinking |
| 4-thio UTP | Modified hybridization | UV-crosslinking |
| 5-iodo CTP | UV-crosslinking | |
| 5-iodo UTP | UV-crosslinking | |
| 5-bromo UTP | UV-crosslinking | |
| 2-chloro ATP | UV-crosslinking | |
| Adenosine 5′-(1-thiotriphosphate) | Chemically unstable | Resistance to nuclease |
| Cytidine 5′-(1-thiotriphosphate) | Chemically unstable | Resistance to nuclease |
| Guanosine-5′-(1-thiotriphosphate) | Chemically unstable | Resistance to nuclease |
| Uridine-5′-(1-thiotriphosphate) | Chemically unstable | Resistance to nuclease |
| Pseudo-UTP | | |
| 5-(3-aminoallyl)-UTP | Post-synthesis modification | |
| 5-(3-aminoallyl)-dUTP | Post-synthesis modification | |

The first agent inhibiting a protein kinase CK2 (CK2) is also a precursor of the double-stranded or single-stranded oligonucleotide as defined above, characterized in that it is selected from the group consisting of:

a) a single-stranded oligonucleotide corresponding to the sense or antisense strand as defined above, b) a double-stranded oligodeoxynucleotide (DNA) corresponding to the sense and/or antisense strands of the double-stranded oligonucleotide as defined above, c) a hairpin oligoribonucleotide comprising the sequences of the sense and antisense RNA strands as defined above, and d) a double-stranded DNA made up of a sense strand corresponding to the DNA equivalent of the oligoribonucleotide defined in e) and of an antisense strand complementary thereto.

For the purpose of the present invention, the expression "DNA equivalent of an RNA sequence" is intended to mean the sequence in which the ribonucleotides (a, g, c, u) of said RNA sequence are replaced with deoxyribonucleotides (a, g, c, t).

The precursors are useful for producing the single-stranded and double-stranded oligonucleotides according to the present invention by the conventional techniques of oligonucleotide synthesis and of transcription using a recombinant vector.

Each of the strands of the siRNA can be synthesized separately and then the complementary strands are hybridized so as to form RNA duplexes. Alternatively, the strands of the siRNA can be synthesized simultaneously.

The siRNA can also be produced in the form of a hairpin RNA molecule according to the principle described in Brummelkamp et al., Science, 2002, 296, 550-553. The hairpin RNA molecule is subsequently cleaved in the cells transfected with said RNA molecule or transduced with an appropriate transcription vector, so as to release the siRNA. This hairpin RNA molecule comprises the sequences of the two strands of the siRNA separated by a short sequence of noncomplementary oligoribonucleotides of approximately 3 to 12 nucleotides forming a loop of approximately 5 to 15 nucleotides. For example, a loop of approximately 10 nucleotides is formed from a short sequence of approximately 8 ribonucleotides and of two nucleotides derived from the 3' end of the sense strand of the siRNA.

The single-stranded and double-stranded oligonucleotides can be either produced by chemical synthesis or by transcription in vitro (test tube) or in cell culture, and then administered in vivo, or they are produced in vivo in the cells of an organism which have been modified with a transcription vector (gene therapy) or a DNA encoding said siRNAs (transgenesis).

The chemical synthesis is carried out according to the conventional phosphoramidite method described in Elbashir et al., Nature, 2001, 411, 494-498. For example, each of the strands of the siRNA can be synthesized according to β-cyanoethyl phosphoramidite chemistry on a solid support using 2'-O-tert-butyldimethylsilyl (TBDMS) as a group for protecting the 2'-position of the ribonucleotide. Other protective groups can be used; silyl ether, which protects the 5'-hydroxyl end of the ribonucleotide, can be used in combination with a labile orthoester which protects the 2'-hydroxyl of the ribonucleotide.

The transcription by means of a recombinant vector uses a double-stranded DNA encoding for at least one or the two strands of the siRNA or else a hairpin RNA as defined above. Such DNAs cloned into appropriate expression vectors allow separate or simultaneous transcription of the two complementary strands of said siRNA, as described, respectively, in Sadher et al., Biochem. Int., 1987: 14, 1015 and in European patent EP 0618 966 in the name of Cis Bio International. For example, the method of preparing double-stranded RNA described in European patent EP 0618 966 uses a DNA template attached to a support which allows the simultaneous transcription of the two RNA strands in the form of double-stranded RNA after a step consisting of amplification (PCR) of the target DNA sequence. The double-stranded RNA obtained can be attached to a support and several different siRNA sequences can be analyzed simultaneously.

The first agent inhibiting a protein kinase CK2 (CK2) consisting in precursor can be inserted in an expression cassette that is characterized in that it comprises at least one precursor as defined above, under the control of appropriate transcriptional regulatory elements, in particular an inducible or non inducible promoter and a transcription terminator.

For the purpose of the invention, an eukaryotic or prokaryotic vector comprising an insert consisting of an oligonucleotide as defined above may be used; preferably, said vector is an expression vector into which an expression cassette as defined above is inserted.

These vectors are constructed and introduced into host cells by conventional recombinant DNA and gene therapy methods, which are known in themselves. Many vectors into which a nucleic acid molecule of interest can be inserted in order to introduce it into and to maintain it in a eukaryotic or prokaryotic host cell are known in themselves; the choice of an appropriate vector depends on the use envisioned for this vector (for example, replication of the sequence of interest, expression of this sequence, maintaining the sequence in extrachromosomal form or else integration into the host's chromosomal material), and also on the nature of the host cell. Use may be made, inter alia, of viral vectors such as adenoviruses, retroviruses, lentiviruses and AAVs into which the sequence of interest has been inserted beforehand, or else nonviral vectors such as plasmids.

Preferably, said vector is a DNA vector (recombinant plasmid or virus) comprising a double-stranded oligodeoxynucleotide as defined above; such a vector encoding an siRNA as defined above is useful for the in vitro or in vivo production of said siRNAs.

Vectors that are particularly suitable for the stable expression of siRNAs are in particular those described in T. R. Brummelkamp et al., Science, 2002, 296, 550-553.

According to another particular embodiment of the combinations according to the present invention, the first agent is 5-(3-chlorophenylamino)benzo[c][2,6]naphthyridine-8-carboxylic acid (CAS 1009820-21-6, called by its commercial name "CX-4945" in the experimental part below), or 5,11-Dimethyl-6H-pyrido[4,3-b]carbazole (CAS 519-23-3, commercially called "Ellipticine"), or 7-Chloro-10-Methyl-11h-Benzo[g]pyrido[4,3-B]indol-3-Ol (described as "compound 18" in the publication of prudent et al., Cancer Research 2010) or 2-Diméthylamino-4,5,6,7-tétrabromo-1H-benzimidazole (DMAT), or 4,5,6,7-tétrabromobenzotriazole (TBBt), or the peptide CIGB300 (Perea et al. Mol Cell Biochem. 2008 September; 316(1-2):163-7). Of course, this list is not limitative, and other CK2 inhibitors can be used according to the present invention. In particular, derivatives of these molecules can be used, provided they exhibit a CK2-inhibiting effect at least as efficient and selective as that of the cited molecules.

Preferably, the first agent is selected from the group consisting of 5-(3-chlorophenylamino)benzo[c][2,6]naphthyridine-8-carboxylic acid and 5,11-Dimethyl-6H-pyrido[4,3-b]carbazole.

According to another particular embodiment of the combinations according to the present invention, the second agent is selected from the group consisting of 2-((2S,6R)-2,6-dimethylmorpholino)-N-(5-(6-morpholino-4-oxo-4H- pyran-2-yl)-9H-thioxanthen-2-yl)acetamide (CAS 925701-49-1, called by its commercial name "KU-60019" in the experimental part below) and 2-Morpholin-4-yl-6-thianthren-1-yl-pyran-4-one (CAS 587871-26-9, called by its commercial name "KU-55933" in the experimental part below). Of course, this list is not limitative, and other ATM kinase inhibitors can be used according to the present invention. In particular, derivatives of the cited molecules can be used, provided they exhibit an ATM kinase-inhibiting effect at least as efficient and selective as that of these molecules.

Preferably, the second agent is 2-((2S,6R)-2,6-dimethylmorpholino)-N-(5-(6-morpholino-4-oxo-4H-pyran-2-yl)-9H-thioxanthen-2-yl)acetamide.

A particular combination according to the present invention is 5-(3-chlorophenylamino)benzo[c][2,6]naphthyridine-8-carboxylic acid as the first agent and 2-((2S,6R)-2,6-dimethylmorpholino)-N-(5-(6-morpholino-4-oxo-4H-pyran-2-yl)-9H-thioxanthen-2-yl)acetamide as the second agent.

In the combinations described above, the first and second agents can be comprised in a composition (in any pharmaceutically acceptable form, such as a pill, tablet, a powder present in a capsule, a liquid etc.), or in a kit of parts. The two agents can also be provided separately, and they will be considered as "combined" in the sense of the present invention as soon as they are administered to a same individual either together or separately, provided the time between the administration of the two agents does not exceed 1 week, preferably 48 hours and more preferable 24 hours.

As mentioned above, the inventors observed a synthetic-lethal interaction between CK2 inhibitors and ATM kinase inhibitors in a VHL null cell line. Further investigations revealed that the observed synergy between the two agents was weaker in cell lines which were not deficient for VHL. Hence, according to a preferred embodiment, a combination according to the present invention is used as a medicament for treating a solid tumor which harbors a VHL inactivation. Examples of such tumors are those which occur in subjects suffering from the von Hippel-Lindau disease, such as hemangioblastomas of the retina and central nervous system, clear cell carcinomas of the kidney, pheochromocytomas, endolymphatic sac tumors, pancreatic islet cell tumors and papillary cystademonas of the epididymis (males) or broad ligament (females), as well as the sporadic counterparts of the tumors observed in VHL disease, such as ccRCC and hemangioblastomas (Kundo and Kaelin, 2001).

Among kidney carcinomas, renal clear cell carcinomas (ccRCC) are the most frequent and the most aggressive ones. According to a particular embodiment, the combination according to the present invention is used as a medicament for treating a renal clear cell carcinoma (ccRCC).

Nephroectomy is the first line of treatment for renal cell carcinoma. The risk of metastasis is high even after kidney nephroectomy, especially when the tumor is VHL$^-$ deficient. Since the synergy between CK2 inhibitor and ATM kinase inhibitor is particularly strong in VHL$^-$ cells, administration of a combination according to the invention is particularly interesting before, during and/or after nephrectomy to prevent the formation of metastases. In metastatic renal cell carcinoma (mRCC), a combination according to the invention is useful to selectively kill metastatic cells, which are VHL$^-$ in a (most often) VHL$^+$ environment. Another aspect of the present invention is hence the use of a combination as above-described, for treating a metastatic renal cell carcinoma (mRCC) or preventing the appearance of metastases.

Another aspect of the present invention is the use of an ATM kinase inhibitor, as a medicament for potentiating the effect of a CK2 inhibitor in the treatment of a cancer which harbors a VHL inactivation. In what precedes, "potentiating" means enhancing the effect of the CK2 inhibitor, so that the combined effect is greater than the sum of the effects of each inhibitor alone, as is the case in synthetic lethality.

Preferred ATM kinase inhibitors which can be used according to this aspect of the invention are 2-((2S,6R)-2,6-dimethylmorpholino)-N-(5-(6-morpholino-4-oxo-4H-pyran-2-yl)-9H-thioxanthen-2-yl)acetamide, 2-Morpholin-4-yl-6-thianthren-1-yl-pyran-4-one and derivatives thereof (as defined above).

The ATM kinase inhibitor is preferably used for potentiating the effect of a CK2 inhibitor selected amongst 5-(3-chlorophenylamino)benzo[c][2,6]naphthyridine-8-carboxylic acid, 5,11-Dimethyl-6H-pyrido[4,3-b]carbazole, 7-Chloro-10-Methyl-11h-Benzo[g]pyrido[4,3-B]indol-3-Ol and derivatives thereof.

According to a preferred embodiment, the ATM kinase inhibitor is preferably used for potentiating the effect of a CK2 inhibitor in the treatment of a cancer selected amongst RCC, ccRCC and mRCC.

Yet another aspect of the present invention is the use of a CK2 inhibitor, for use as a medicament for potentiating the effect of an ATM kinase inhibitor in the treatment of a cancer which harbors a VHL inactivation.

Preferred CK2 inhibitors used according to this aspect of the invention are 5-(3-chlorophenylamino)benzo[c][2,6]naphthyridine-8-carboxylic acid, 5,11-Dimethyl-6H-pyrido[4,3-b]carbazole, 7-Chloro-10-Methyl-11h-Benzo[g]pyrido[4,3-B]indol-3-Ol, 2-Diméthylamino-4,5,6,7-tétrabromo-1H-benzimidazole, 4,5,6,7-tétrabromobenzotriazole and derivatives thereof.

The CK2 inhibitor is used for potentiating the effect of an ATM kinase inhibitor which is preferably selected amongst 2-((2S,6R)-2,6-dimethylmorpholino)-N-(5-(6-morpholino-4-oxo-4H-pyran-2-yl)-9H-thioxanthen-2-yl)acetamide, 2-Morpholin-4-yl-6-thianthren-1-yl-pyran-4-one and derivatives thereof.

According to a preferred embodiment, the CK2 inhibitor is used for potentiating the effect of an ATM kinase inhibitor in the treatment of a cancer selected from RCC, ccRCC and mRCC.

The present invention will be understood more clearly from the further description which follows, which refers to examples illustrating the effect of the combined inhibition of ATM kinase and CK2 on cultured cells, as well as to the appended figures.

B) shCTRL 786-O cells were treated with indicated concentrations of ATM inhibitor, KU-55933 (white bars), CX-4945 (grey) or both (black) for 48 h and cell viability was measured as in A. * represents p=0.03, between the sum of % cell growth inhibition of ATMi and CX-4945 vs the Mix of both.

C) Two different ATM inhibitors (ATM inhibitor KU-60019 (Sellekchem) and ATM inhibitor KU-55933, CAS 587871-26-9 (Calbiochem)) were used to study their synergetic effect with two different inhibitors of CK2 (CX-4945 or Ellipticine) on 786-O cell viability ●: ATM inhibitor; □: CK2 inhibitor; Δ: both). Upper left panel: CX-4945 and KU-55933; Upper right panel: CX-4945 and KU-69001; Lower left panel: Ellipticine and KU-60019. Cell viability was measured and represented as percentage of viability compared to cells treated with the vehicle (DMSO) taken as 100%.

Figure 3:
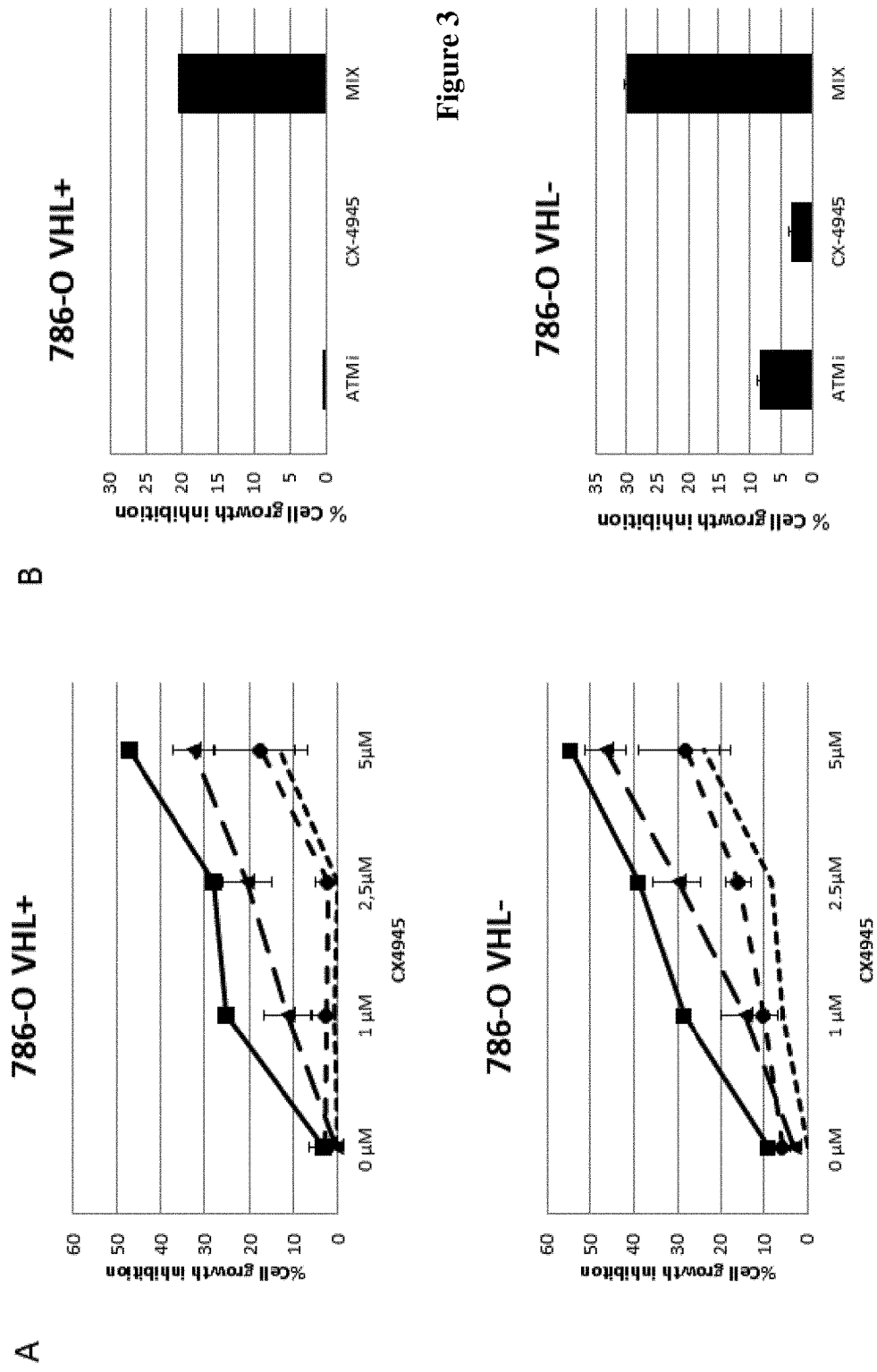

FIG. 3: A) 786-O cells (VHL$^+$ upper panel and VHL$^-$ lower panel) culture under 20% $O_2$ (Normoxia) were treated with increasing concentrations of CX-4945 in the absence (dotted line) or in the presence of KU-60019 (ATMi), dashed lines with circle 2.5 μM, triangle 5 μM and plain line with square 10 μM) for 48 h. Cell death was measured and represented as a percentage compared to DMSO taken as 0%.

B) Cell growth inhibition of 786-O cells (VHL$^+$ upper panel and VHL$^-$ lower panel) upon treatment with 5 μM KU-60019 or 2.5 μM CX-4945 or both (MIX: 0.5μM KU60019+2.5 μM CX-4945) under normoxia.

FIG. 4: A) 786-O cells (VHL$^+$ upper panel and VHL$^-$ lower panel) cultured under 1.5% $O_2$ (Hypoxia) were treated with increasing concentrations of CX-4945 in the absence (dotted line) or in the presence of KU-60019 (ATMi), 2.5 μM (dashed line with circle), 5 μM (dashed line with triangle) and 10 μM (plain line with square) for 48 h. Cell death was measured and represented as a percentage compared to DMSO taken as 0%.

B) Cell growth inhibition of 786-O cells (VHL$^+$ upper panel and VHL$^-$ lower panel) upon treatment with 5 μM KU-60019 or 2.5 μM CX-4945 or both (MIX: 5μM KU-60019+2.5 μM CX-4945) under hypoxia. ** represents p=0.019.

C) Caki-2 cells were treated under normoxia (lower panel) or hypoxia (upper panel) with indicated concentrations of KU-60019 in the absence or in the presence of 2.5 or 5 μM (white, grey and black bars respectively) of CX-4945 for 48 h. Cell viability was measured and represented as a percentage of cell death compared to DMSO, taken as 0%. * represents p=0.16.

D) RPTEC cells were treated under normoxia (lower panel) or hypoxia (upper panel) with indicated concentrations of KU-60019 in the absence or in the presence of 2.5 or 5 μM (white, grey and black bars respectively) of CX-4945 for 48 h. Cell viability was measured and represented as a percentage of cell death compared to DMSO, taken as 0%. "Add mix" corresponds to the difference between the measured effect of the combination of the two inhibitors and a theoretical value corresponding to the addition of the effect measured for each inhibitor separately.

Figure 5:
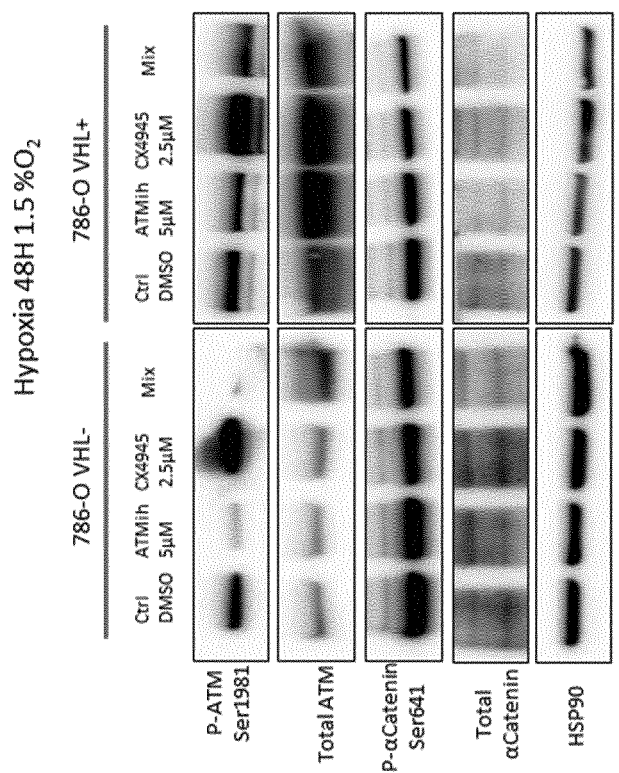

FIG. 5: 786-O cells (VHL$^-$ and VHL$^+$) cultured under 1.5% $O_2$ (Hypoxia) were treated for 48 h with DMSO (CTRL), 5 μM KU-60019 (ATMi), 2.5 μM CX-4945 or both (mix). Expression (total) and phosphorylation (P-) of ATM and αCatenin were assessed by Western blot. HSP90 was used as a loading control.

Figure 6:
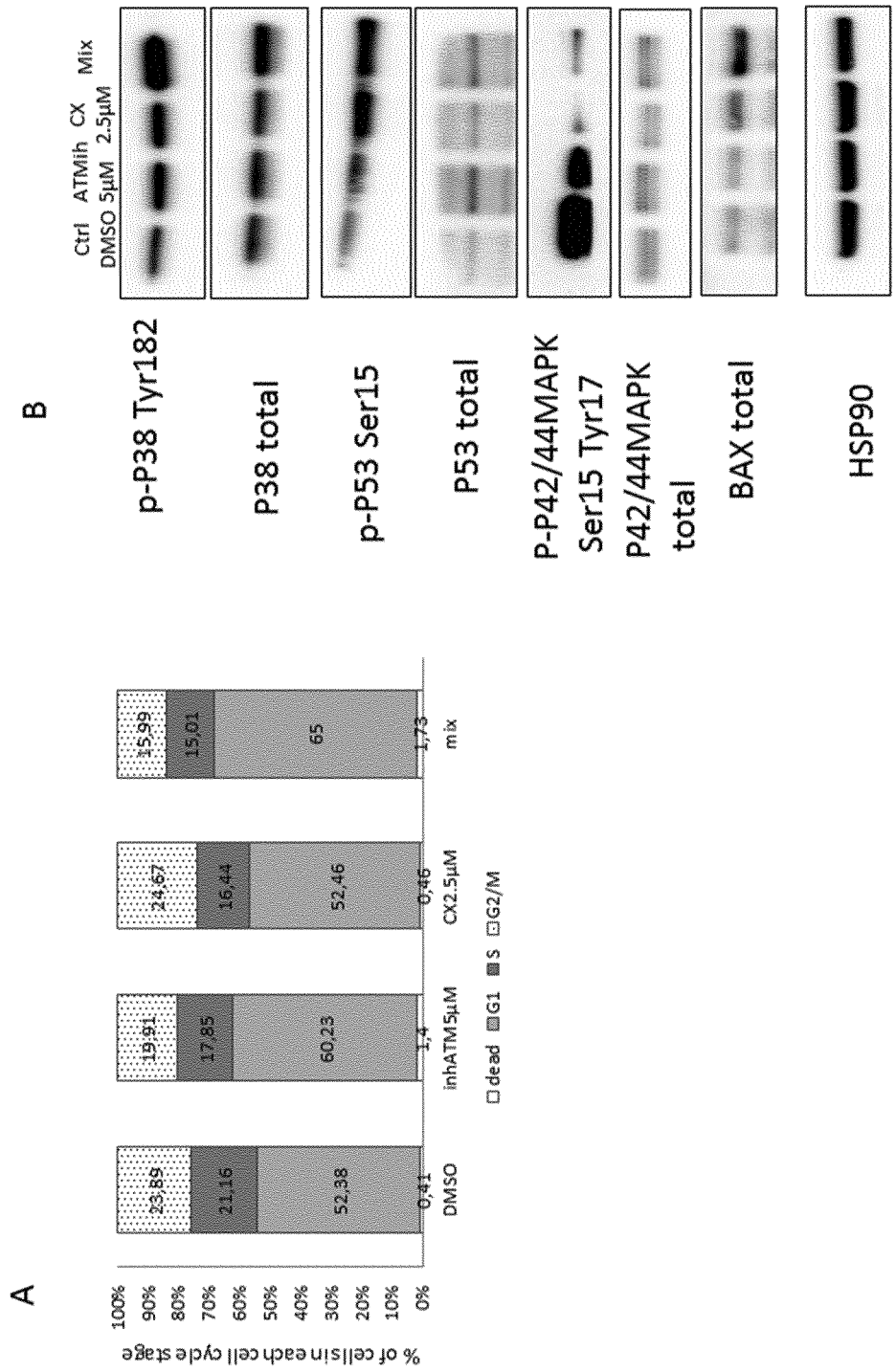

FIG. 6: A) FACS analysis of 786-O VHL$^-$ cells treated for 48 h with indicated compounds under hypoxic conditions and labeled with Propidium Iodide for cell cycle analysis.

B) Western blot analysis of 786-O VHL$^-$ cells treated for 48 h with indicated compounds under hypoxic conditions. HSP90 was used as a loading control.

Figure 7:
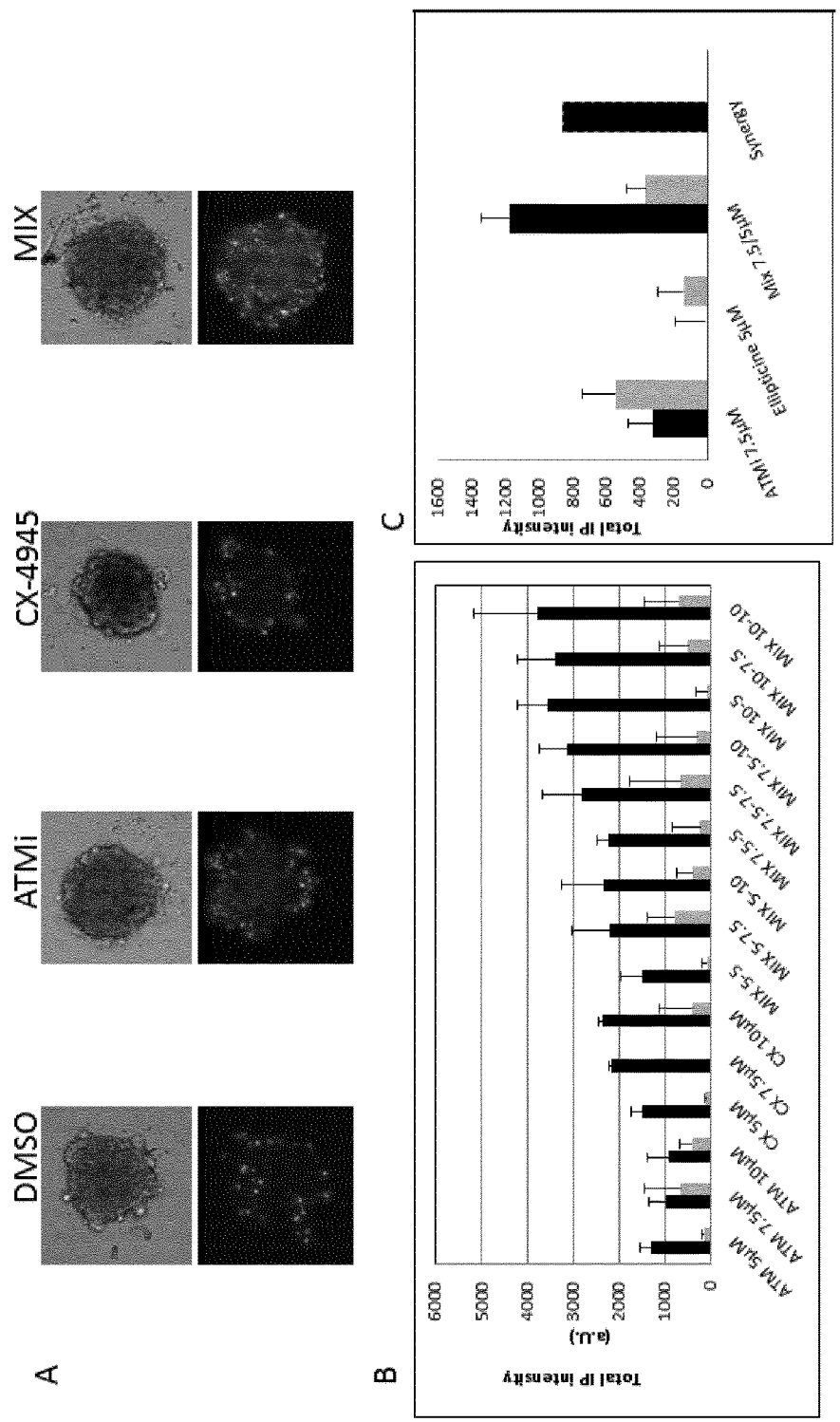

FIG. 7: 786-O VHL$^-$ cells were seeded on poly-Hema precoated U-bottom wells, grown for 3 days followed by 48 h of treatment as indicated. A) Dead cells were visualized using Propidium Iodide.

B and C) Acquisitions and analysis were performed on ArrayScan$^{VTI}$ (ThermoScientific).

Figure 8:
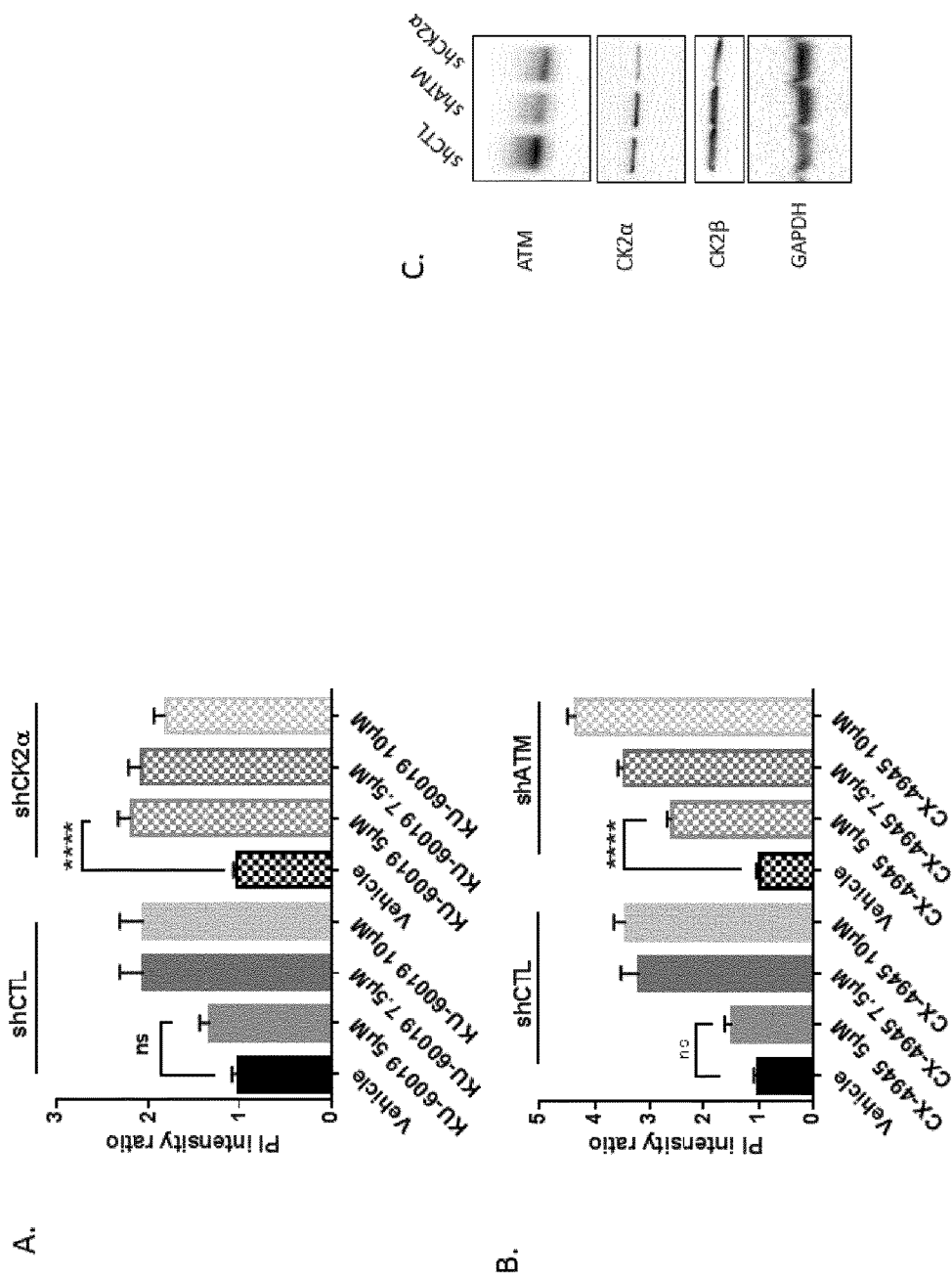

FIG. 8: Cell death was monitored by Propidium Iodide quantification as described in Materials and Methods (in 3D assay). A) 786-O shCTL and 786-O shCK2α MTS were treated with vehicle or increasing concentrations of KU-60019 (5, 7.5 and 10 μM). CTL means "control".

B) 786-O shCTL and 786-O shATM MTS were treated with vehicle or increasing concentrations of CX-4945 (5, 7.5 and 10 μM)

C) Western Blot analysis of the indicated cell lines with antibodies against ATM, CK2α, CK2β and GAPDH as loading control.

Figure 9:
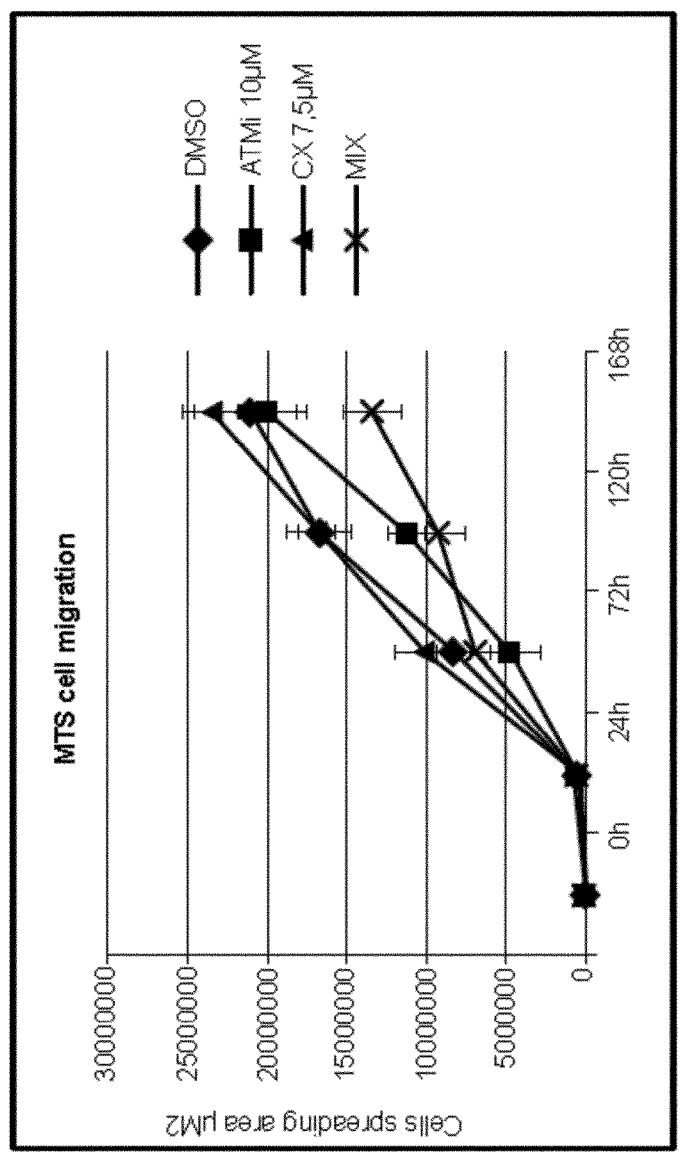

FIG. 9: Spheroid migration assay: spheroids were grown as previously described for 3 days and then seeded in flat bottom tissue culture plates and treated with DMSO, KU-60019 (ATMi), CX-4945 (CX) or both (mix) at time that correspond to 0 h. Pictures were taken at indicated time points and area occupied by the spreading cells was measured using ImageJ. Student test between ATMi and mix at 168 h is <0.05.

Figure 10A:
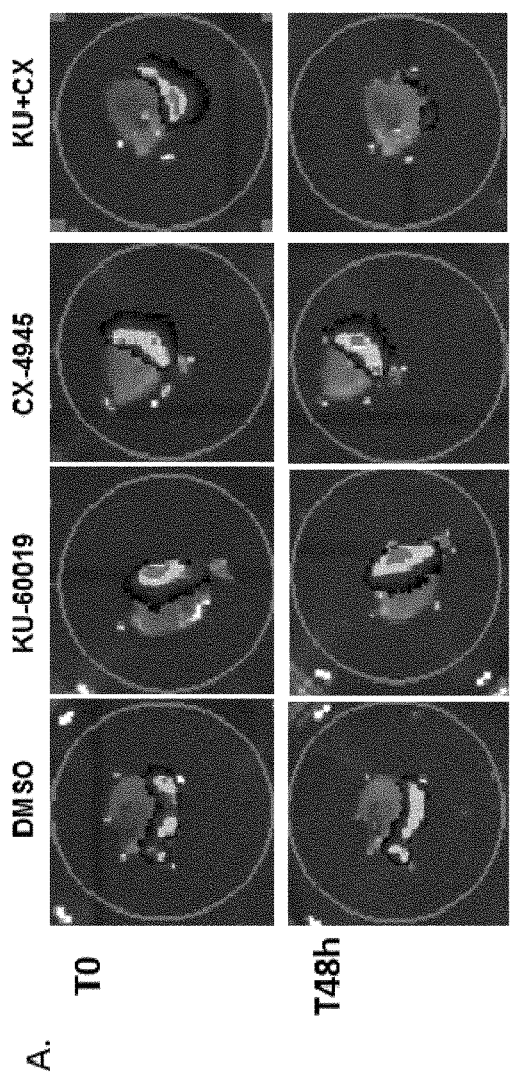
Figure 10A:
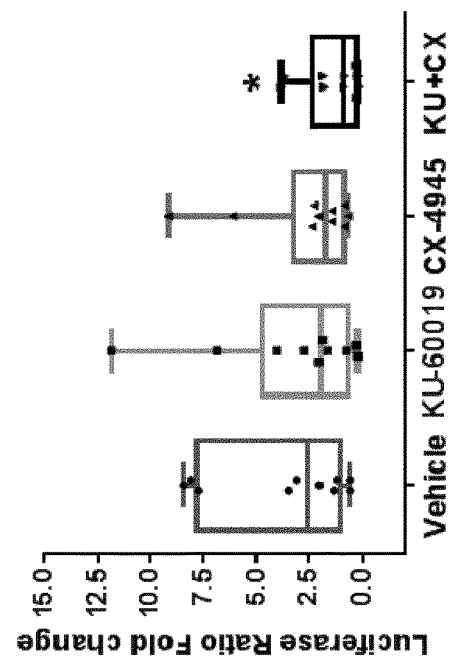
Figure 10B:
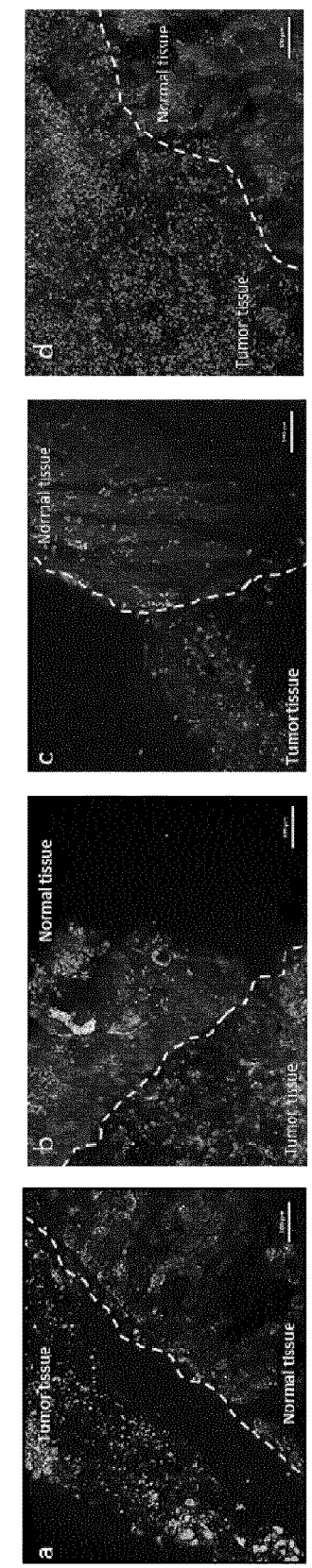

FIG. 10: A) 786-O-Luc cells (3 millions) were injected under renal capsula. 4 weeks grown orthotropic mice kidney tumours were cut in slices (300 μm) and treated with either Vehicle (DMSO), KU-60019 (10 μM), CX-4945 (10 μM) or combination of both during 48 h. Injected 786-O LUC cells were followed and Luciferase emission was measure. Picture A, before and after treatments. Right panel: Luciferase ratio fold changes on each condition compared to changes in the Control after 48 hours of treatments (* p<0.05). Mann-Whitney test.

B) Tissue slices cultures (300 μm of thickness) carrying tumour and normal kidney tissue (indicated in the pictures) were marked with Live and Dead Kit (ThermoFisher) after 48 h of treatments with a. Vehicle; b. KU-60019 10 μM c. CX-4945 10 μM and d. KU 10 μM+CX10 μM. Red marker intensity (Ethidium Bromide=dead cells) was measured on both normal and tumor areas on images taken with an Apotome-equipped Zeiss microscope. B1, Lower left panel: Significant difference was observed between KU-60019 (*p≤0.0001), CX-4945 (p≤0.001) alone versus KU+CX (Mann-Whitney test for all describe conditions) (CTL vs MIX=***, here not represented); B2, Right Panel: PI intensity in normal tissue shows no significant difference when comparing each condition alone versus the mix of drugs. Bar scale 100 μm.

Figure 11:
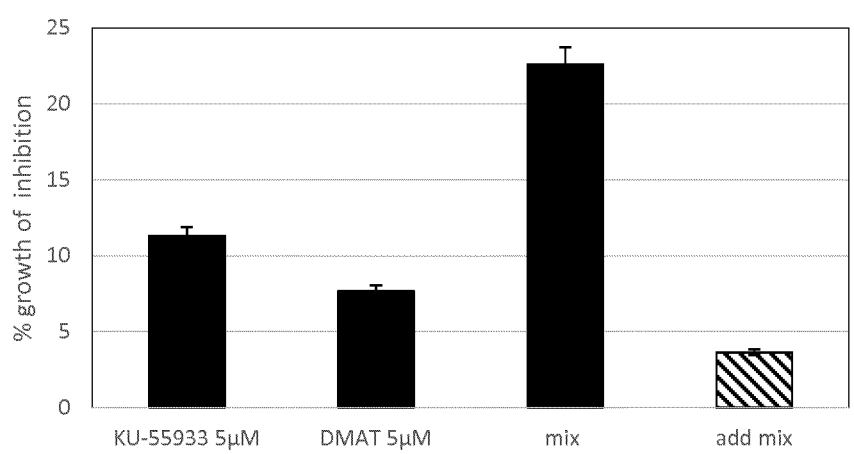
Figure 11:
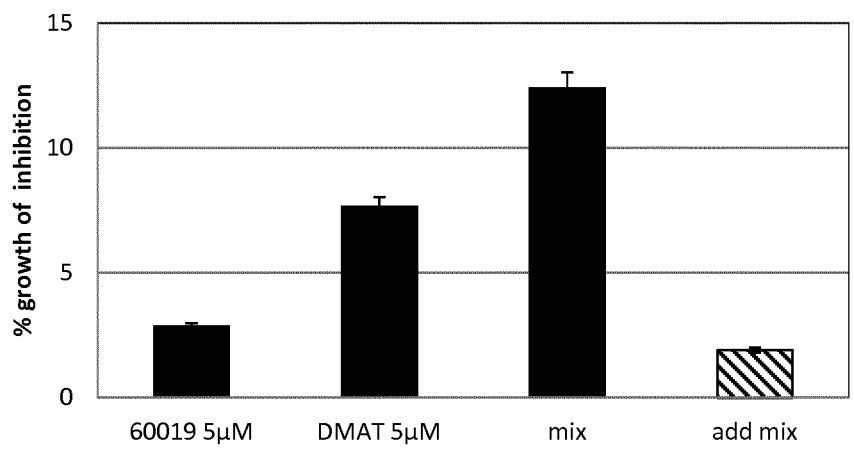

FIG. 11: 786-O cells were treated with indicated inhibitors for 48 h. Cell viability was measured and represented as a percentage of growth inhibition compared to DMSO, taken as 0%. "Add mix" corresponds to the difference between the measured effect of the combination of the two inhibitors and a theoretical value corresponding to the addition of the effect measured for each inhibitor separately.

A) KU55933 at 5 μM and DMAT at 5 μM.

B) KU60019 at 5 μM and DMAT at 5 μM.

EXAMPLE 1

Materials and Methods

Chemicals

All compounds were dissolved in pure DMSO at a concentration of 10 mM. CX-4945 was synthesized at the *Plateau Synthèse Organique, Département de Chimie moléculaire*, UJF, Grenoble, according to the method described by (Pierre, Chua et al. 2010). The chemical library was composed of 2 commercial libraries, one from ENZO (screen-well kinases inhibitors) and the other from Selleckchem (Tyrosine kinase inhibitors) that were complemented with other inhibitors (see Table V).

containing 10% of fetal bovine calf serum, penicillin [100 U/mL], streptomycin [100 µg/mL] was used for the RCC4 cells and McCoy's medium containing 10% of fetal bovine

TABLE V chemical library

| Molecules | Target | Molecules | Target | Molecules | Target | Molecules | Target |
|---|---|---|---|---|---|---|---|
| U0126 | MEK | PHA665752 | MET | CHIR 99021 | GSK3b | Lapatinib | EGFR |
| AG370 | PDGF R | AT9283 | AURORA A/B | Tyrphostin 25 | EGFR | TSU 68 | TGFbR/FGF R1 |
| SP600125 | JUNK | TIE 2 | ANGR | ML-7 | MLCK | CP 690550 | JAK3 |
| GEFITINIB | EGFR | GDC0941 | PI3K | Rapamycin | mTOR | STF 62247 | autophagy inducer |
| SUNITINIB | VEGFR | Roxolitinib | JAK/STAT | OSI 930 | cKIT | Baraseritib | |
| APATINIB | VEGFR | RG1462 | EGFR | KRN633 | VEGFR | AG 490 | JAK2 |
| DOXORUBICIN | Topoisomerase | H89 | PKA | GSK 1838705 | IGFR | SU 4312 | FLK1 |
| VEMURAFENIB | ERK | Kempollone | GDK3b | TGFb R inhib | TGFbR | Bosutinib | ABL |
| SB203580 | P38 MAPK | SU11274 | MET | ATM inhib | ATM | Pazopanib | VEGFR |
| LY294002 | PI3K | AG490 | EGFR | Piceatannol | SYK | AZ 960 | JAK |
| INDIRUBIN | GSK3b | PF562271 | FAK | Roscovitine | CDK | CX4945 | CK2 |
| PF2341066 | MET | Iniparib | PARP | Axitinib | VEGFR & PDGFR | Temsirolimus | mTOR |
| SXG523 | MET | Enzastaurin | PKC | Imatinib | ABL | Aurora 1 inhib | AURORA A |
| WP1130 | DUB/ABL | Tyrphostin 1 | CTRL inactif | INCB018424 | JAK/STAT | AG 126 | IRAK |
| FASENTIN | GLUT1 | KN62 | CamK | Crenolanib | PDGFR alpha | GW 5074 | cRAF |
| YM155 | Sirvivin | BML257 | AKT | Saracatinib | SRC | Dasatinib | ABL |
| LAVENDUSTIN | EGFR | NVP-ADW742 | IGF1R | GSK1120212 | MEK | Sorafenib | VEGFR |
| HYPERICIN | PKC | MK1775 | WEE1 | PP1 | SRC | Cyt 387 | JAK |
| Y27632 | ROCK | KX2-391 | SRC | ZM 336372 | cRAF | 5FU | ADN |
| Paclitaxel | Tubuline | Perifosine | AKT | AZD 0530 | SRC/ABL | Tosasertib | Aurora |

Lentiviral particles were provided by Sigma-Aldrich coming from the PLKO1 vector Hpgk-puro-cMV-tGFP, containing different shRNA sequences targeting different genes (see Table VI).

TABLE VI genes targeted by shRNA

| Gene | Accession Number | Gene | Accession Number |
|---|---|---|---|
| PDK1 | NM_002610 | BCL2A1 | NM_004049 |
| PLK2 | NM_006622 | TP53 | NM_000546 |
| PNCK | NM_198452 | ATM | NM_000051 |
| HCK | NM_002110 | ATR | NM_001184 |
| NEK6 | NM_014397 | CHEK1 | NM_001274 |
| TRIB3 | NM_021158 | CHEK2 | NM_007194 |
| PCTK3/CDK18 | NM_002596 | MAPK14 | NM_001315 |
| MET | NM_000245 | CDK6 | NM_001259 |
| MELK | NM_014791 | PTK2 | NM_005607 |
| AURKB | NM_004217 | SRC | NM_198291 |
| KIT | NM_000222 | PAX2 | NM_000278 |
| PRKCD | NM_006254 | CSF1R | NM_005211 |
| PXK | NM_017771 | FGFR1 | NM_015850 |
| PDGFRL | NM_006207 | CA9 | NM_001216 |
| LCK | NM_005356 | AURORA | NM_003600 |
| PIM2 | NM_006875 | FLT1 | NM_002019 |
| MAPK1 | NM_138957 | CSNK2A1 | NM_001895 |
| AURKB | NM_004217 | CSNK2B | NM_001320 |

Sh-CTL corresponds to the empty vector Hpgk-puro-cMV-tGFP;
Sh-CK2α corresponds to the vector Hpgk-puro-cMV-tGFP cloned with sequence CAATTGTACCAGACGTTAA (SEQ ID NO: 87);
Sh-ATM corresponds to the vector Hpgk-puro-cMV-tGFP cloned with sequence TGATGGTCTTAAGGAACATCT (SEQ ID NO: 88).

Cell Culture ccRCC cell lines 786-O, RCC4 and Caki-2 as well as normal renal proximal tubular epithelial cell line RPTEC were obtained from ATCC and Evercyte (Germany), respectively. Cells were grown in 10-cm diameter plates in a humidified incubator (37° C., 5% $CO_2$) with RPMI 1640 medium (Gibco) containing 10% of fetal bovine calf serum, penicillin [100 U/mL], streptomycin [100 µg/mL] concerning 786-O. DMEN medium Glutamax 4.5 mg/mL (Gibco)

calf serum, penicillin [100 U/mL], streptomycin [100 µg/mL] was used for the Caki-2 cell line.

RPTEC were cultured in ProXup (Evercyte). 786-O and Caki2 cells were passed every 2-3 days and only once a week for RPTEC.

The parental VHL null cell line was used to generate its derivative lines containing either the empty expression vector HA-pBABE or a functional VHL construct HA-VHL (VHL$^+$ cells). Stable transfectants were maintained in medium supplemented with 2 µs/ml puromycin.

Transduction of shRNA in 786-O Cells

For infection, 786-O cells were plated into 6 well-plates ($8 \times 10^5$ in 2 mL of serum-supplemented RPMI 1640 medium). The day after, adherent cells were incubated with lentiviral particles (1-5 MOI) diluted in 1000 µl of serum-supplemented medium containing 8 µg/µL polybrene. After 4 h, 1 mL of medium was added to cultures and transduction was maintained for 16 hours before washing cells and changing the medium. For stable transduction, puromycin selection started 36 h post-infection (at the concentration of 2 µg/mL) and was maintained during all cell culture.

Spheroids Culture

For 3-D culture (spheroids), the spheroids were prepared in 96-wells U-bottom tissue culture plate with low evaporation Lid (Microtest™, Becton Dickinson Labware, San Jose, Calif.) coated with 20 mg/mL of poly-HEMA per well to allow the formation of spheroids. Renal cancer cells 786-O WT, 786-O pBABE and 786-O VHL (taken from exponentially growing cultures) were seeded at a density of $1 \times 10^3$ cells/mL in RPMI supplemented with 10% FCS. 90 µL ($9 \times 10^2$ cells) of these cell suspensions were deposed in each well then tissue culture plates were incubated at 37° C. and 5% $CO_2$ for 3 days before drug treatment for further 48 h.

Viability Assay

Cytotoxicity was measured using PrestoBlue assay (Invitrogen, Carlsbad, Calif.). Cell lines were seeded in a 96-well microtiter plate at a concentration of $5\times10^4$ cells/mL. Cells were allowed to attach for 24 hrs at 37° C. and 5% $CO_2$. The cells were exposed to the negative control DMSO or positive drug CX-4945 at 20 µM for 48 h or the other molecules at indicated concentrations.

Western Blot Analysis

Cells were lysed in RIPA buffer containing a cocktail of protease and phosphatase inhibitors (Tris HCl pH 7.4 10 mM, NaCl 150 mM, SDS 0.1%, Na Deoxycholate 0.5%, EDTA 1 mM, Triton X100 1%, containing a protease inhibitor cocktail (Sigma P8340), phosphatase inhibitor cocktails 1 and 2 (Sigma P2850, P5726), 15 min and clarified at 16,000 g for 15 min. Homogenates were quantified using BCA protein Assay kit (Thermo Scientific). SDS-PAGE was performed using pre-cast 4-12% gradient gel (Bio-Rad) and electrophoresed in NuPAGE buffer at 150 volts for 75 minutes. Separated proteins at 20 µg/lane were transferred to PVDF membranes (60 minutes at 100 Volts). Blotted membranes were blocked during 1 h at room temperature with saturation buffer (1% BSA in TBST), and then incubated with primary antibody diluted in saturation buffer, during 1 h 30. Secondary antibodies were added for 1 hour. Detection was achieved by using Luminata Forte Western HRP substrate (Millipore) and Fusion FX acquisition systems. Anti-βactin (Abcam), GAPDH (Ambion) or HSP90 (Cell Signaling) were used to control for equal protein loading.

Fully Automated, High-Throughput Screening Assay

In 96-well plates, 90 µl of either Ctrl- or targeted-shRNA expressing 786-O cell suspension ($55.5\times10^3$ cells/ml) were seeded and plates incubated overnight in a 5% $CO_2$, 37° C., humidified atmosphere. Then, 10 µl of each compound was added at the indicated concentrations (1, 5 or 20 µM final concentration) using the CMBA's robotic platform. DMSO was used as a negative control and 20 µM CX-4945 as a positive control. Plates were further cultured for 48 hrs. Cells were labeled with vital Hoechst (33342) together with Prestoblue and the fluorescence reading was made through the Tecan's Infinite M100 reader. See Flow chart in FIG. 1.

Data Processing and Hit Selection

Primary and secondary High-Throughput Screening assays were evaluated and validated using a simple statistical parameter, the Z'-factor (Zhang, Chung et al. 1999).

Raw data were first imported into the database of the home-made analysis software TAMIS, used for analysis. For each test plate and assay type (PrestoBlue or vital Hoechst), mean of the eight DMSO negative control values was considered as 0% activity and mean of the eight CX-4945 positive control values was considered as 100% activity. Then, each compound X-related raw values were translated in activity percent, compared to DMSO (0%) and CX-4945 (100%). Finally, for each compound X/targeted-shRNA Y pair and assay, the activity percentage obtained with the compound X/Ctrl-shRNA was taken from the compound X/targeted-shRNA Y activity percentage in order to identify compound X/targeted-shRNA Y pair showing additive, or even synergistic, effect compared to compound X/Ctrl-shRNA pair.

Statistical Analysis

All value were expressed as mean±SEM. The statistical significance between groups was determined using GraphPad Prism v6.0d.

3D Assay

Three days pre-formed spheroids were treated with the different drugs at indicated concentrations during 48 H. After that, Hoechst (200 ng/mL) and Propidium Iodide (1 µg/mL) were added as markers of cell nuclei and cell death respectively. Images of IP and Hoechst fluorescence were acquired at the CMBA platform using the automated microscope ArrayScanVTI (ThermoScientific). ArrayScanVTI is a fluorescent microscope which allows the rapid and fully automated acquisition of images of fixed or live cells in 96-well microplates at different magnifications. Dedicated softwares are used to automatically perform High Content image Analysis like spheroid area measurement, fluorescent intensity measurement of each staining and counting of the number of dead cells.

Cell Migration Assay

Cell migration assay was performed as described in Gunter et al (2003). After 3 days of stationary culture in polyHema coated round bottom 96 wells plate, individual multicellular spheroids were placed in 96 flat bottom well culture plates and treated either with DMSO, CX-4945, KU-60019 or the MIX of both. Upon adherence to the solid support, spheroids disassembled and released cells migrated away radially from their initial position. Cells were marked with Hoechst and images were taken with AXIObserver ZEISS microscope. The area covered by cells was measured every 24 h over a period of 7 days. The area covered by the cells was taken as an indicator of cellular migration ability.

Ex Vivo Models

Orthotopic Xenograft Tumor Model in Mice

All animal studies were approved by the institutional guidelines and those formulated by the European Community for the Use of Experimental Animals. Four- to 6-week-old BALB/c nude mice (Charles River Laboratories) with a mean body weight of 18-20 g were used to establish orthotopic xenograft tumor models. The mice were housed and fed under specific pathogen-free conditions. To produce tumors, renal cancer cells 786-O luc were harvested from subconfluent cultures by a brief exposure to 0.25% trypsin-EDTA. Trypsinization was stopped with medium containing 10% FBS, and the cells were washed once in serum-free medium and resuspended in 500 µL PBS. Renal orthotopic implantation was carried out by injection of 3×106 786-O luc cells into the right kidney of athymic nude mice. Seven week after implantation, the xenografted kidney was remove to prepare tissue slices.

Fresh Tissue Sectioning

A Vibratome VT1200 (Leica Microsystems) was used to cut thin (300-500 µm) slices from fresh tissue (see Xenograft tumor model). Samples were soaked in ice-cold sterile balanced salt solution, orientated, mounted, and immobilized using cyanoacrylate glue. Slicing speed was optimized according to tissue density and type; in general, slower slicing speed was used on the softer tissues and vice versa (0.03-0.08 mm/neoplastic tissue; 0.01-0.08 mm/s normal tissue). Vibration amplitude was set at 2.95-3.0 mm.

Organotypic Tissue Cultures

Tissue slices were cultured on organotypic inserts for up to 120 h (one slice per insert; Millipore). Organotypic inserts are Teflon membranes with 0.4-µm pores that allow preservation of 3D tissue structure in culture. Tissue culture was performed at 37° C. in a 5% $CO_2$ humidified incubator using 1 ml of DMEM media supplemented with 20% inactivated FBS (GIBCO), 100 U/mL penicillin (Invitrogen) and place in a rotor agitator to allow gas and fluids exchanges with the medium. The tissue slices were harvested at baseline time (T0) and thereafter, at 24-h intervals; the slices were incubated with the drugs at the indicated concentrations and after 24 h and 48H, medium-containing Luciferin was added to image luminescence of cancer cells 786-O luc using IVIS.

ROI levels allowed quantifying the efficacy of the drug treatment. Alternatively, cell viability of the slices was assayed using Live&Dead Kit (Promega) as recommended.

Results

Figure 1:
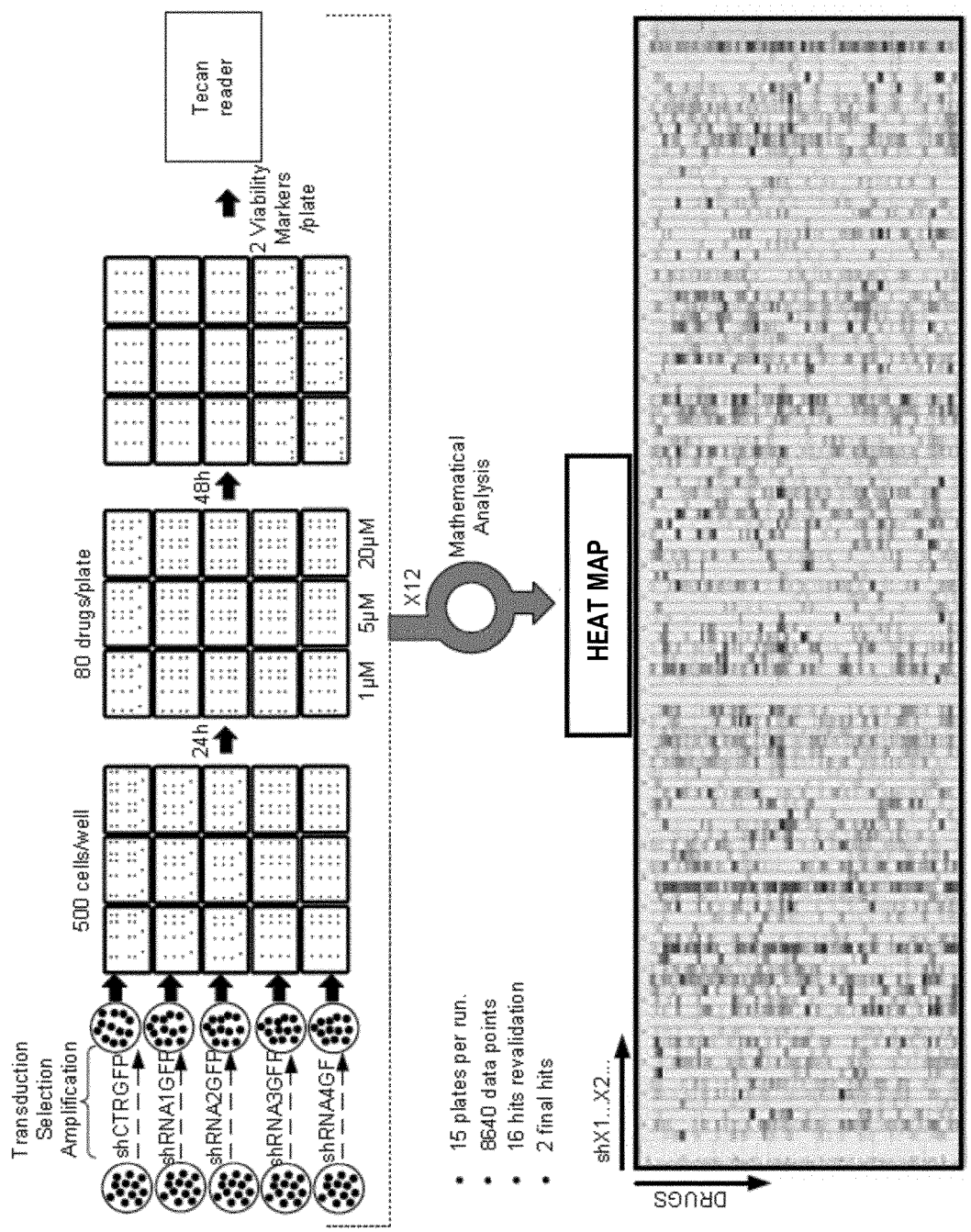
FIG. 1: Flow chart of the screening.

As a first step to identify potential novel therapeutic targets in ccRCC, the screening platform was used to interrogate drug-gene interactions using the 786-O VHL$^-$ cell line. Cancer-relevant genetic aberrations were selected using literature and database search. This yielded a list of 36 genes that have been linked to several cancers including ccRCC (Table VI). To assess the effect of inhibition of these genes in cancer, the inventors manipulated their expression using RNA interference (RNAi). The chemical library mainly consisted of clinically relevant kinase inhibitors (including a series of FDA-approved therapeutics) that altogether comprised 80 small molecules (Table V). Next, to search for drug-gene interactions, the inventors have established a multiplexed assay to analyze the cellular fitness of the shRNA-engineered cell lines in response to the chemical library. This method enabled to query a 36×80 drug-gene matrix, which allowed the interrogation of almost 2,880 drug-gene pairs. The library was screened at three concentrations, yielding over 8,640 data points (FIG. 1). As mentioned before, cell viability markers were used to measure the effects of each combination in each cell line versus the control.

Figure 2A:
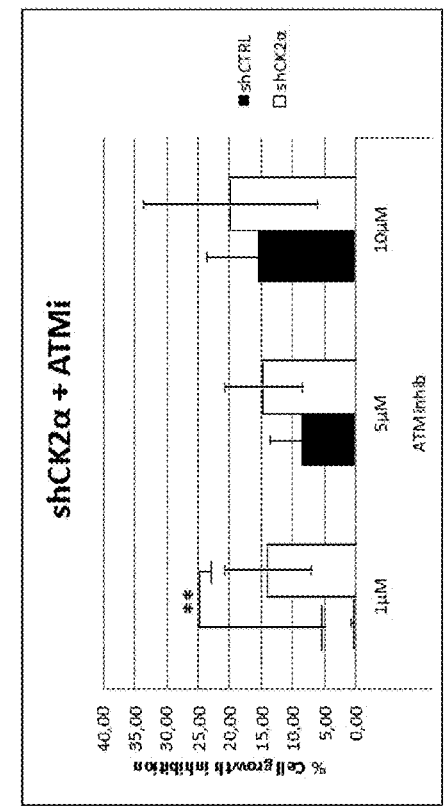
FIG. 2: A) Indicated transfected 786-O cells (shCTRL in black and shCK2α in white) were treated with 1, 5 or 10 μM of ATM inhibitor, KU-55933 for 48 h. Cell viability was measured and represented as a percentage of growth inhibition compared to DMSO, taken as 0%. * represents p=0.44. CTRL means "control".
Figure 2B:
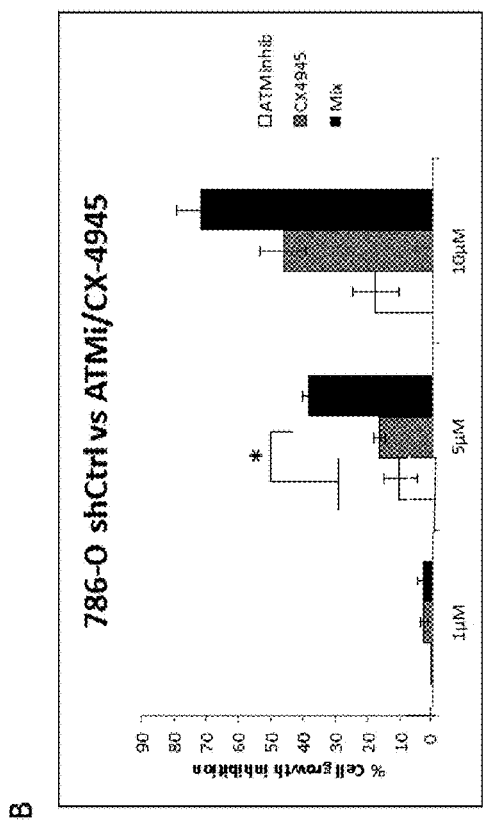
Figure 2C:
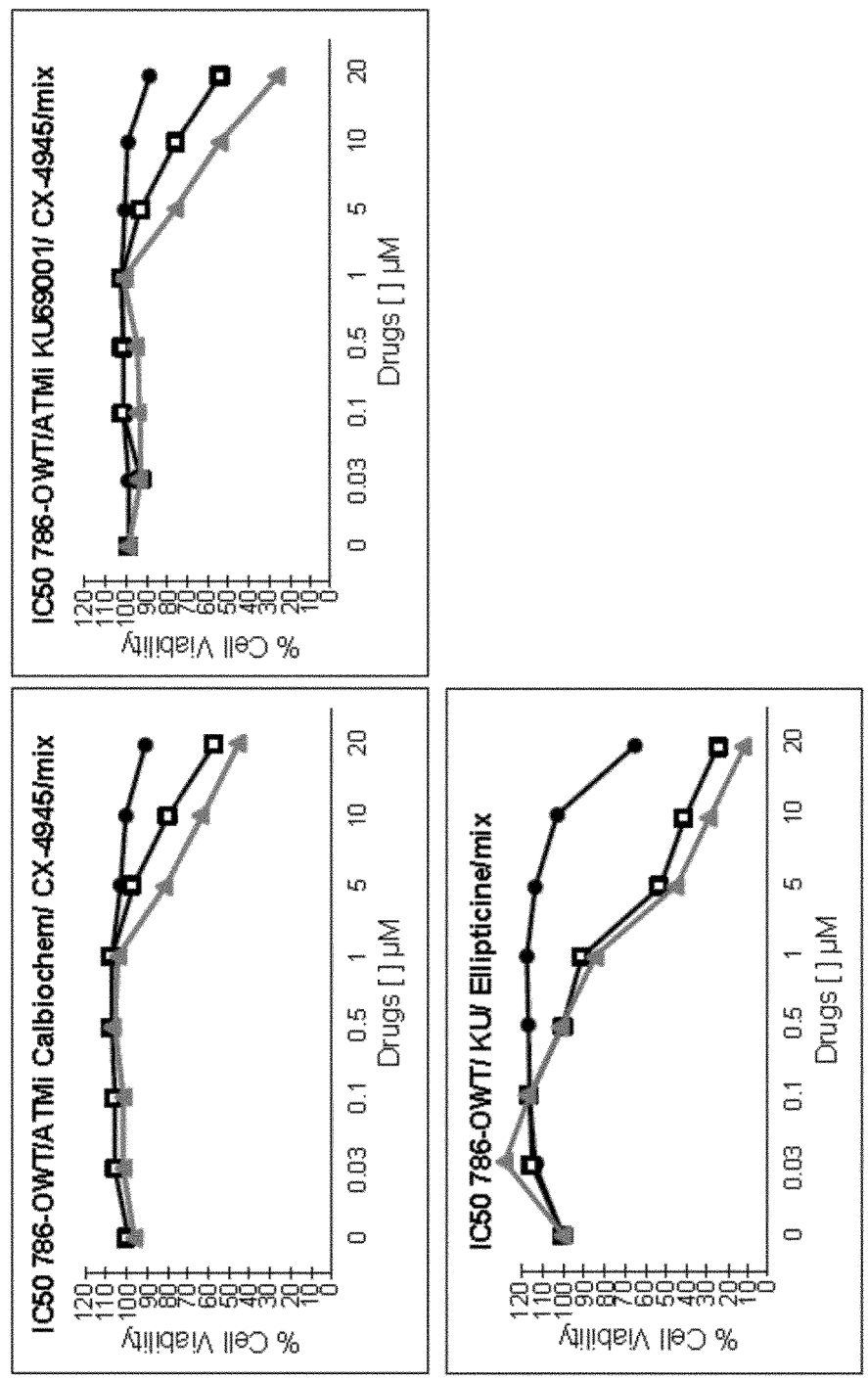
Figure 4A:
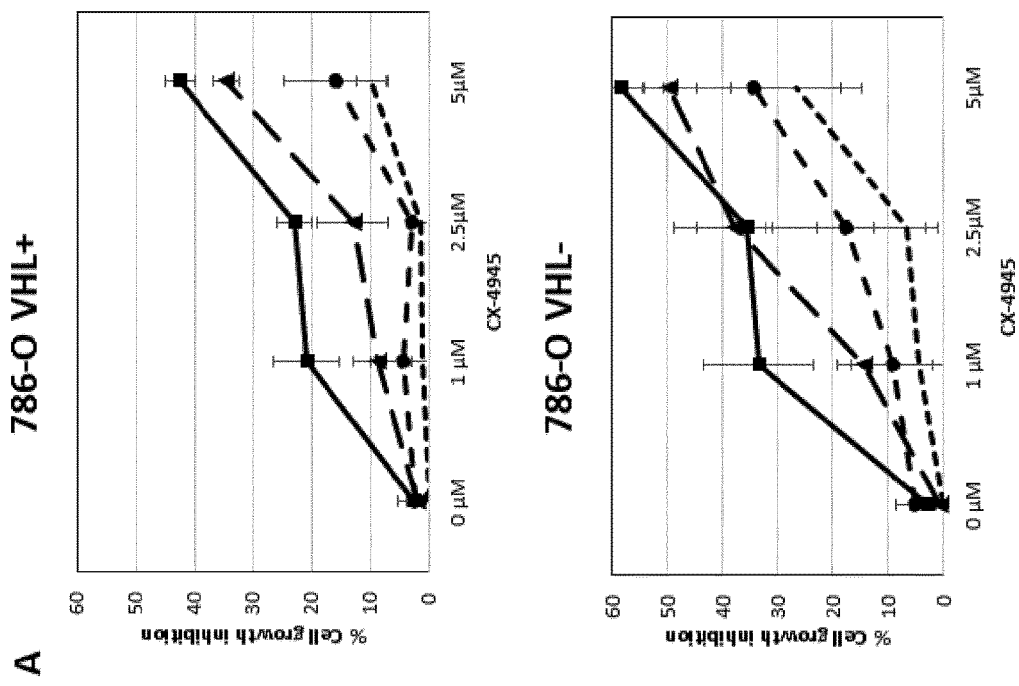
Figure 4B:
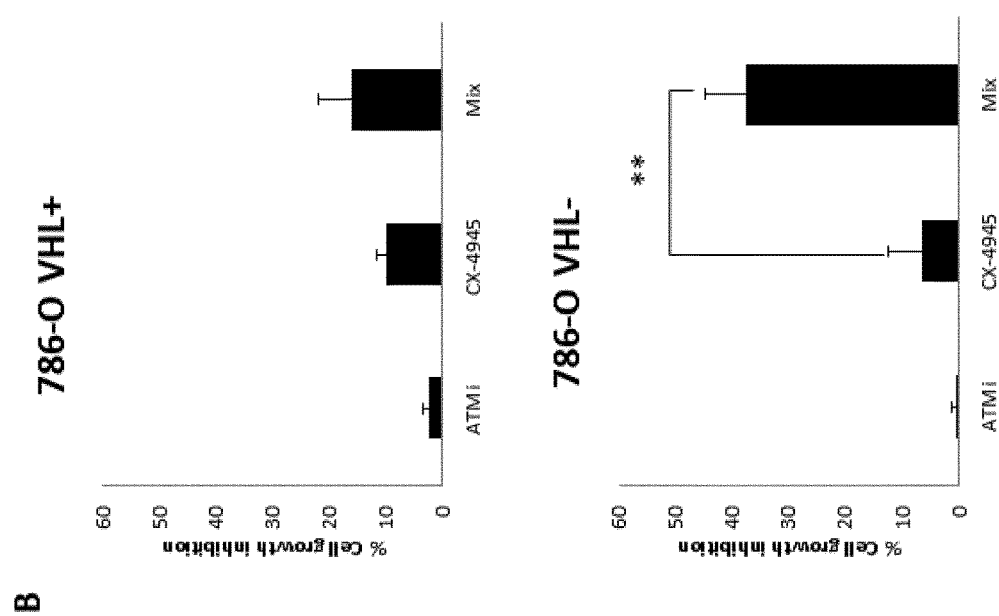

Data analysis revealed several gene-drug interactions including synthetic-lethal interactions between components of signaling pathways and specific kinase inhibitors. Among them, the inventors found that the shRNA-mediated knockdown of CK2α expression enhanced the sensitivity of 786-O VHL$^-$ cells to an inhibitor of Ataxia Telangiectasia Mutated (ATM) kinase KU-55933 (Calbiochem) (FIG. 2A). The same synergistic effect was also observed when the cells were treated with a combination of ATM inhibitor KU-55933 plus CX-4945, a protein kinase CK2 inhibitor, suggesting a synthetic-lethal interaction (FIG. 2B). To confirm the specificity of the targeted-kinases, the inventors used another ATM inhibitor KU-60019 (from Selleckchem) as well as another CK2 inhibitor named Ellipticine (FIG. 2C). As KU-60019 showed to be significantly more efficient, this ATM inhibitor was used in the follow up experiments. The inventors then stably reintroduced the tumor suppressor VHL in 786-O cells and measured the sensitivity of these cells to the CK2 and ATM inhibitors. They found that the synergistic anti-proliferative effect of the combination was much stronger in 786-O VHL$^-$ cells as compared to 786-O VHL$^+$ cells (FIG. 3A, B). One of the roles of VHL is to promote the degradation of HIF factors under normoxic conditions. Indeed, VHL complex tags HIF-1α with ubiquitin and thereby marks it for degradation by the 26S proteasome. It is admitted that in tumor, the cell environment is hypoxic. Consequently, it has been previously shown that there are differences in drug effects due to different VHL status in hypoxic conditions. Thus, the inventors looked at the effect of the CK2 and ATM inhibitors in low oxygen (1.5%). As illustrated in FIG. 4AB, 786-O VHL$^+$ cultured and treated under hypoxic conditions are less sensitive to each inhibitor alone. However, the most striking observation was the strong synergetic effect of the combination in the VHL$^-$ cells as compared to the VHL$^+$ cells. The calculated theoretical additive cell death effect of both inhibitors was ~10% whereas the observed effect was 37%, clearly indicating a synthetic lethality process.

Figure 4C:
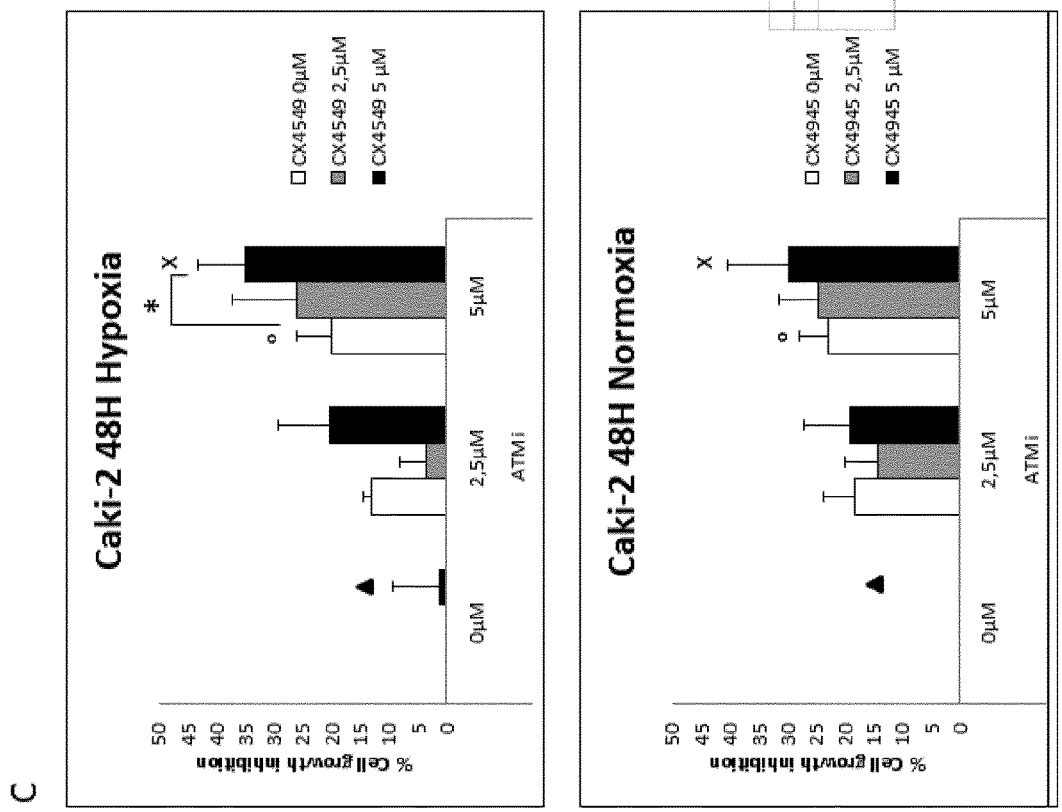
Figure 4D:
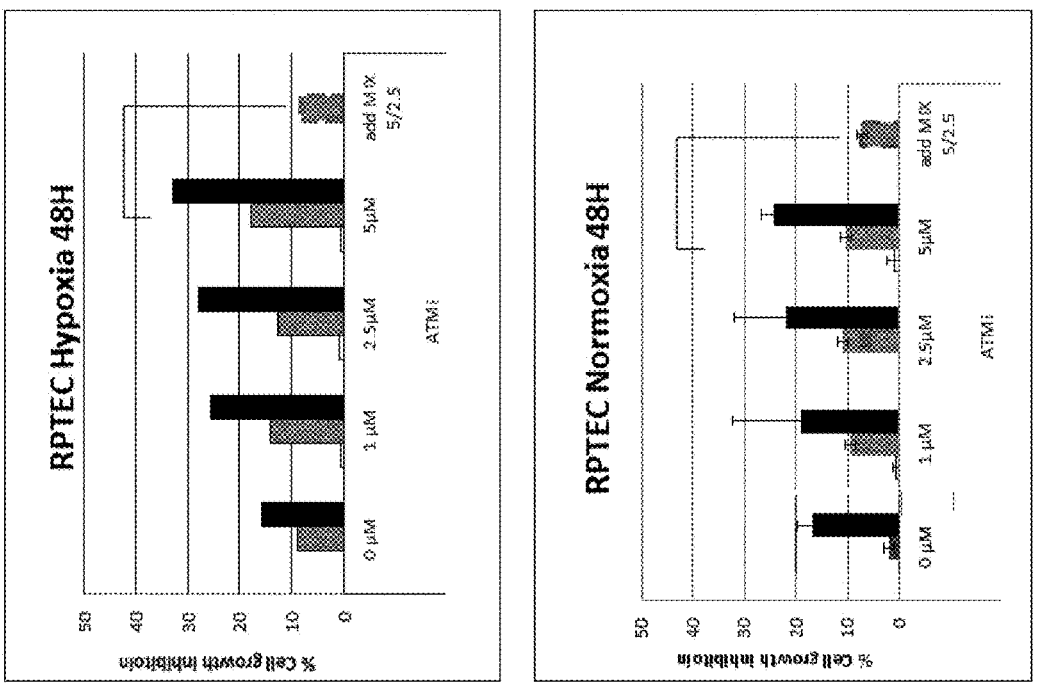

Caki2 cell line was isolated from primary ccRCC and has a loss-of-function mutation in the von Hippel-Lindau (VHL) tumor-suppressor protein. These cells are known to form tumors in immunocompromised mice. In VHL mutated form of ccRCC cells like Caki2, this synergetic effect was also present (FIG. 4C). As comparison, RPTEC that are described as "normal" renal epithelial cells, are as sensitive to these inhibitors as 786-O VHL$^+$ cells (FIG. 4D) in normoxic conditions and some more sensitive in hypoxic conditions, suggesting a role of HIF in this response.

Western blot analysis was performed to visualize the inhibition, in hypoxic conditions, of ATM and CK2 in 786-O cell lines by KU-60019 and CX-4945, respectively (FIG. 5). ATM was clearly inhibited by KU-60019 in VHL$^{+/-}$, 1.5% O$_2$ conditions, as evidenced by reduction in the canonical phosphorylation of P-ATM Ser1981. The same was observed for CK2 in 786-O VHL$^-$, using P-α-Catenin Ser641. Surprisingly, substrates phosphorylation was less affected in the mix both in normoxia and hypoxia.

To understand how cell viability might be affected by the treatments, the inventors looked for apoptosis markers. Neither PARP cleavage nor caspase activation were detected, indicating that the inhibitors did not induce apoptosis (data not shown). Cell cycle analysis was performed by FACS using Propidium Iodide labeling. FIG. 6A shows that there was barely detectable cell death induced by the combination of inhibitors (1.73%) as compared to control (0.46%). However, the G1 phase was extended in cells where ATM was inhibited, whereas CX4945 was without effect. Moreover, the combination of ATM and CK2 inhibitors increased the amount of G1-arrested cells (65%), while decreasing cells in S and G2/M phases (15 and 16% respectively) as compared to DMSO treated cells. These data were confirmed by Western blot analysis of proliferation-related markers (p38 MAPK and p42/p44 MAPK) as well as cell cycle arrest markers (P53 and BAX) (FIG. 6B).

In order to be closer to the tumor environment, the drug treatments were performed in Multicellular Tumor Spheroids (MTS), which are known to mimic micro-tumors more closely than cancer cell line monolayers. Indeed, MTS represent quite realistically the 3-D growth and organization of solid avascular tumors and consequently simulate more precisely the cell-cell interactions and micro-environmental conditions found in tumors, especially nutrient and oxygen gradients. Several studies indicated that drug sensitivity testing performed on Tumor spheroids can effectively predict the efficiency of new antitumor compounds in patients and has proven in numerous studies to be of tremendous interest in characterizing the effects of chemotherapeutics (Dubessy, Merlin et al. 2000). In that context, Tumor spheroid models are particularly interesting as they reproduce the multicellular resistance (MCR) associated to cell-cell interaction, low drug penetration, resistance of quiescent cells located in the deepest and hypoxic regions (Desoize 2000, Hirschhaeuser, Menne et al, 2010). Tumor spheroids generated from 786-O VHL$^-$ cells were treated for 48 h with ATM or CK2 inhibitors or with their combination. As shown in FIG. 7, 10 µM ATM inhibitor KU-60019 and 7.5 µM CX-4945 were the optimal concentrations that show a synergetic effect on the viability of 786-O VHL$^-$ cells, as visualized by propidium iodide staining.

Multicellular Tumor Spheroids (MTS) were pre-formed for 3 days with indicated 7856-O sh-transduced cell lines before treatment for 48 h with vehicle or drugs. Significant difference (**** P≤0.0001) was observed when comparing the treatment of either shCK2α MTS with Vehicle (DMSO) to 5 µM KU-60019 or shATM MTS with vehicle to 5 µM CX-4945 (Kruskal-Wallis non-parametric test) (FIGS. 8A and 8B). Western Blot analysis of stable shATM and shCK2α cell lines showing decreased protein expression levels of either ATM or CK2α after shRNA transduction and selection. CK2β levels do not change, showing specificity of shRNA against CK2α. Loading was normalized using GAPDH (FIG. 8C).

This assay shows that any combination of ATM inhibitor and CK2α inhibitor efficiently decrease viability of tumor cells.

To assess the effect of the combined inhibitors on the migration capacity of cancer cells, the inventors performed spheroid migration assay. The preliminary data shown in FIG. 9 suggest that only the combination of the two inhibitors impair the cell spreading of treated spheroids.

Co-Inhibition of CK2α and ATM Induces Cell Death in Ex Vivo Models

The majority of preclinical kidney cancer research is based on established cell lines. However, these cell lines frequently have undergone multiple changes influencing their biological behavior and therefore no longer reflect the primary tumor of origin. Freshly isolated primary epithelial cells, in contrast, may be more closely related to the malignant epithelial cells of the tumor. But it is most likely that separated tumor cells will behave differently in vitro, as both cell-cell and cell-matrix interactions are highly different compared to the in vivo situation. Therefore, to investigate tumor cell behavior ex viva, it is necessary to maintain or reconstitute an environment closely resembling the tumor tissue.

To achieve this, the inventors took advantage of their expertise in cutting pre-induced xenografts of kidney tumors (Vaira, Fedele et al. 2010). Briefly, 786-O Luciferase cells were injected under the kidney capsule of nude mice and tumor growth was monitored through Luciferase intensity using an IVIS Imaging reader. After 6 weeks of growth, mice were euthanized and tissue slices were generated from the tumors using a Vibratome (Leica). Tissue slices were placed in special supports that allow oxygen-gas exchange and were treated for 48 h at different drug concentrations. Read-out of the drug effect on tumor slices was performed in vivo using either immunofluorescence (cell live & dead kit) or Luciferase activity measurement with IVIS Imaging reader (FIG. 10).

In conclusion, considering that the CK2 inhibitor CX-4945 is currently evaluated for the treatment of several types of cancers, the above findings reveal a strategy to potentially improve the efficacy of CK2 inhibition in RCC by co-treatment with ATM inhibitors. There is a strong preclinical rationale to combine CK2 and ATM inhibitors to treat advanced stage RCC, with immediate implications for clinical evaluation.

EXAMPLE 2

Materials and Methods

Chemicals

All compounds were dissolved in pure DMSO at a concentration of 10 mM. DMAT (Catalog No. 218699) and KU-55933 (Catalog No. 118500) are from Calbiochem and KU-60019 (Catalog No. S1570) is from Selleckchem.

Cell Culture ccRCC cell lines 786-O was obtained from ATCC and was grown in 10-cm diameter plates in a humidified incubator (37° C., 5% $CO_2$) with RPMI 1640 medium (Gibco) containing 10% of fetal bovine calf serum, penicillin [100 U/mL], streptomycin [100 µg/mL].

Viability Assay

Cell lines were seeded in a 96-well microtiter plate at a concentration of $5 \times 10^4$ cells/mL. Cells were allowed to attach for 24 hrs at 37° C. and 5% $CO_2$. The cells were exposed to the negative control DMSO or indicated molecules for 48 h in hypoxic conditions (1.5% $O_2$, 5% $CO_2$ at 37° C.). Cytotoxicity was measured using PrestoBlue assay (Invitrogen, Carlsbad, Calif.).

Results

Inventors tested several combinations of CK2α inhibitors as first agent and ATM inhibitors as second agent.

Among them, results of a combination with 2-Diméthylamino-4,5,6,7-tétrabromo-1H-benzimidazole (DMAT) and KU-60019 or KU-55933 on the inhibition of cell growth are represented in FIG. 11.

A same synergistic effect was observed when the cells were treated with a combination of DMAT with KU-60019 and DMAT with KU-55933.

These results confirm that the combination of a CK2α inhibitor and a ATM inhibitor is efficient on cell growth inhibition.

REFERENCES

Brummelkamp et al., Science, 2002, 296, 550-553 Desoize, B. (2000). "Contribution of three-dimensional culture to cancer research." Crit Rev Oncol Hematol 36(2-3): 59-60.

Dubessy, C., J. M. Merlin, C. Marchal and F. Guillemin (2000). "Spheroids in radiobiology and photodynamic therapy." Crit Rev Oncol Hematol 36(2-3): 179-192.

Elbashir et al., Nature, 2001, 411, 494-498.

Figlin, R., C. Sternberg and C. G. Wood (2012). "Novel agents and approaches for advanced renal cell carcinoma." J Urol 188(3): 707-715.

Golding Sarah E. et al, Improved ATM kinase inhibitor KU-60019 radiosensitizes glioma cells, compromises insulin, AKT and ERK prosurvival signaling, and inhibits migration and invasion; Mol Cancer Ther October 2009 8; 2894

Günther W, Pawlak E, Damasceno R, Arnold H and A J. Terzis (2003). "Temozolomide induces apoptosis and senescence in glioma cells cultured as multicellular spheroids." Br J Cancer. 2003 Feb. 10; 88(3):463-9.

Hirschhaeuser, F., H. Menne, C. Dittfeld, J. West, W. Mueller-Klieser and L. A. Kunz-Schughart (2010). "Multicellular tumor spheroids: an underestimated tool is catching up again." J Biotechnol 148(1): 3-15.

Kundo, K. and Kaelin, W. G. (2001). "The von Hippel-Lindau Tumor Suppressor Gene." Experimental Cell Research 264, 117-125.

Lopez-Beltran, A., M. Scarpelli, R. Montironi and Z. Kirkali (2006). "2004 WHO classification of the renal tumors of the adults." Eur Urol 49(5): 798-805.

Maj-Hes, A., 3. Medioni, F. Scotte, M. Schmidinger, G. Kramer, P. Combe, Y. Gornadha, R. Elaidi and S. Oudard (2013). "Rechallenge with mTOR inhibitors in metastatic renal cell carcinoma patients who progressed on previous mTOR inhibitor therapy." Oncology 85(1): 8-13.

Marschke Robert F. et al, Abstract C39: Phase I clinical trial of CX-4945: A first-in-class orally administered small molecule inhibitor of protein kinase CK2; Mol Cancer Ther December 2009 8; C39

McDermott, D. F., M. M. Regan, J. I. Clark, L. E. Flaherty, G. R. Weiss, T. F. Logan, J. M. Kirkwood, M. S. Gordon, J. A. Sosman, M. S. Ernstoff, C. P. Tretter, W. J. Urba, J. W. Smith, K. A. Margolin, J. W. Mier, J. A. Gollob, J. P. Dutcher and M. B. Atkins (2005). "Randomized phase III trial of high-dose interleukin-2 versus subcutaneous interleukin-2 and interferon in patients with metastatic renal cell carcinoma." J Clin Oncol 23(1): 133-141.

McLornan, D. P., A. List and a J. Mufti (2014). "Applying synthetic lethality for the selective targeting of cancer." N Engl J Med 371(18): 1725-1735.

Negrier, S., B. Escudier, C. Lasset, J. Y. Douillard, J. Savary, C. Chevreau, A. Ravaud, A. Mercatello, J. Peny, M. Mousseau, T. Philip and T. Tursz (1998). "Recombinant human interleukin-2, recombinant human interferon alfa-2a, or both in metastatic renal-cell carcinoma. Groupe Francais d'Immunotherapie." N Engl J Med 338(18): 1272-1278.

Perea S E., Reyes O., Baladron I., Perera Y., Farina H., Gil J., Rodriguez A., Bacardi D., Marcelo J. L., Cosme K., Cruz M., Valenzuela C., López-Saura P. A., Puchades Y., Serrano J. M., Mendoza O., Castellanos L., Sanchez A., Betancourt L., Besada V., Silva R., López E., Falcón V., Hernández I., Solares M., Santana A., Díaz A., Ramos T., López C., Ariosa J., González L. J., Garay H., Gómez D., Gómez R., Alonso D. F., Sigman H., Herrera L., Acevedo B. (2008). "CIGB-300, a novel proapoptotic peptide that impairs the CK2 phosphorylation and exhibits anticancer properties both in vitro and in vivo." Mol Cell Biochem. 316(1-2):163-7.

Pierre, F., P. C. Chua, S. E. O'Brien, A. Siddiqui-Jain, P. Bourbon, M. Haddach, J. Michaux, J. Nagasawa, M. K. Schwaebe, E. Stefan, A. Vialettes, J. P. Whitten, T. K. Chen, L. Darjania, R. Stansfield, K. Anderes, J. Bliesath, D. Drygin, C. Ho, M. Omori, C. Proffitt, N. Streiner, K. Trent, W. G. Rice and D. M. Ryckman (2010). "Discovery and SAR of 5-(3-Chlorophenylamino)benzo[c][2,6]naphthyridine-8-carboxylic acid (CX-4945), the first clinical stage inhibitor of protein kinase CK2 for the treatment of cancer." J Med Chem 54(2): 635-654.

Prudent R, Moucadel V, Nguyen C H, Barette C, Schmidt F, Florent J C, Lafanechère L, Sautel C F, Duchemin-Pelletier E, Spreux E, Filhol O, Reiser J B and C. Cochet (2010). "Antitumor activity of pyridocarbazole and benzo-pyridoindole derivatives that inhibit protein kinase CK2." Cancer Res. 2010 Dec. 1; 70(23):9865-74.

Sadher et al., Biochem. Int., 1987: 14, 1015.

Siddiqui-Jain et al., "CX-4945, an orally bioavailable selective inhibitor of protein kinase CK2, inhibits prosurvival and angiogenic signaling and exhibits antitumor efficacy"; Cancer Res Dec. 15, 2010 70; 10288.

Vaira, V., G. Fedele, S. Pyne, E. Fasoli, G. Zadra, D. Bailey, E. Snyder, A. Faversani, G. Coggi, R. Flavin, S. Bosari and M. Loda (2010). "Preclinical model of organotypic culture for pharmacodynamic profiling of human tumors." Proc Nati Acad Sci USA 107(18): 8352-8356.

Vecchio, D. et al, (2014), Predictability, efficacy and safety of radiosensitization of glioblastoma-initiating cells by the ATM inhibitor KU-60019. Int. J. Cancer, 135: 479-491.

Zhang, J. H., T. D. Chung and K. R. Oldenburg (1999). "A Simple Statistical Parameter for Use in Evaluation and Validation of High Throughput Screening Assays." J Biomol Screen 4(2): 67-73.

The invention claimed is:

1. A method of treating a solid tumor containing a VHL inactivation in a human subject comprising administering a combination of a first agent inhibiting a protein kinase CK2 (CK2) and a second agent inhibiting an Ataxia Telangiectasia Mutated (ATM) kinase.

2. The method of claim 1, wherein said first agent is selected from the group consisting of molecules inhibiting the kinase activity of CK2, siRNAs targeting a gene encoding CK2α and/or α' and shRNAs targeting a gene encoding CK2α and/or α', and said second agent is selected from the group consisting of molecules inhibiting the kinase activity of ATM kinase, siRNAs targeting a gene encoding ATM kinase and shRNAs targeting a gene encoding ATM kinase.

3. The method of claim 1, wherein said first agent is selected from the group consisting of 5-(3-chlorophenylamino)benzo[c][2,6]naphthyridine-8-carboxylic acid, 5,11-Dimethyl-6H-pyrido[4,3-b]carbazole, 7-Chloro-10-Methyl-11h-Benzo[g]pyrido[4,3-B]indol-3-Ol, 2-Diméthylamino-4,5,6,7-tétrabromo-1H-benzimidazole and 4,5,6,7-tétrabromobenzotriazole.

4. The method of claim 1, wherein said second agent is selected from the group consisting of 2-((2S,6R)-2,6-dimethylmorpholino)-N-(5-(6-morpholino- 4-oxo-4H-pyran-2-yl)- 9H-thioxanthen-2-yl)acetamide, 2-Morpholin-4-yl-6-thianthren-1-yl-pyran-4-one.

5. The method of claim 1, wherein said first agent is selected from the group consisting of 5-(3-chlorophenylamino)benzo[c][2,6]naphthyridine-8-carboxylic acid and 5,11-Dimethyl-6H-pyrido[4,3-b]carbazole and said second agent is 2-((2S,6R)-2,6-dimethylmorpholino)-N-(5-(6-morpholino-4-oxo-4H-pyran-2-yl)-9H-thioxanthen-2-yl)acetamide.

6. The method of claim 1, wherein said first agent is 5-(3-chlorophenylamino)benzo[c][2,6]naphthyridine-8-carboxylic acid and said second agent is 2-((2S,6R)-2,6-dimethylmorpholino)-N-(5-(6-morpholino-4-oxo-4H-pyran-2-yl)-9H -thioxanthen-2-yl)acetamide.

7. The method of claim 1, wherein said first and second agents are comprised in a composition or in a kit of parts.

8. The method of claim 1 wherein the solid tumor is renal clear cell carcinoma (ccRCC).

9. The method of claim 8, wherein said ccRCC is a metastatic renal cell carcinoma (mRCC).

10. The method of claim 1, wherein the ATM kinase inhibitor is administered in an amount effective to potentiate the effect of a CK2 inhibitor.

11. The method of claim 10, wherein the ATM kinase inhibitor is selected from the group consisting of 2-((2S, 6R)-2,6-dimethylmorpholino)-N-(5-(6- morpholino-4-oxo-4H-pyran-2-yl)-9H-thioxanthen-2-yl)acetamide, 2-Morpholin-4-yl-6-thianthren-1-yl-pyran- 4-one.

12. The method of claim 10, wherein the CK2 inhibitor is selected from the group consisting of 5-(3-chlorophenylamino)benzo[c][2,6]naphthyridine-8-carboxylic acid, 5,11-Dimethyl-6H-pyrido[4,3-b]carbazole, 7-Chloro-10-Methyl-11h-Benzo[g]pyrido[4,3-B]indol-3-Ol, 2-Diméthylamino-4,5,6,7-tétrabromo-1H-benzimidazole and 4,5,6,7-tétrabromobenzotriazole.

13. The method of claim 10 wherein the solid tumor is selected from the group consisting of RCC, ccRCC and mRCC.

14. The method of claim 1, wherein the CK2 inhibitor is administered in an amount effective to potentiate the effect of an ATM kinase inhibitor.

15. The method of claim 14, wherein the CK2 inhibitor is selected from the group consisting of 5-(3-chlorophenylamino)benzo[c][2,6]naphthyridine-8-carboxylic acid, 5,11-Dimethyl-6H-pyrido[4,3-b]carbazole, 7-Chloro-10-Methyl-11h-Benzo[g]pyrido[4,3-B]indol-3-Ol, 2-Diméthylamino-4,5,6,7-tétrabromo-1H-benzimidazole and 4,5,6,7-tétrabromobenzotriazole.

* * * * *

SEQUENCE LISTING

```
<160> NUMBER OF SEQ ID NOS: 88

<210> SEQ ID NO 1
<211> LENGTH: 21
<212> TYPE: DNA
<213> ORGANISM: Mus musculus

<400> SEQUENCE: 1
aagcagggcc agagtttaca c                                              21

<210> SEQ ID NO 2
<211> LENGTH: 21
<212> TYPE: DNA
<213> ORGANISM: Mus musculus

<400> SEQUENCE: 2
aacacacaca gaccccgaga g                                              21

<210> SEQ ID NO 3
<211> LENGTH: 21
<212> TYPE: DNA
<213> ORGANISM: Mus musculus

<400> SEQUENCE: 3
cagaccccga gagtactggg a                                              21

<210> SEQ ID NO 4
<211> LENGTH: 21
<212> TYPE: DNA
<213> ORGANISM: Mus musculus

<400> SEQUENCE: 4
aatttgagag gtgggcccaa c                                              21
```

```
<210> SEQ ID NO 5
<211> LENGTH: 21
<212> TYPE: DNA
<213> ORGANISM: Mus musculus

<400> SEQUENCE: 5
aatgtccgag ttgcttctcg a                                           21

<210> SEQ ID NO 6
<211> LENGTH: 21
<212> TYPE: DNA
<213> ORGANISM: Mus musculus

<400> SEQUENCE: 6
tgtggagctt gggttgtatg c                                           21

<210> SEQ ID NO 7
<211> LENGTH: 20
<212> TYPE: DNA
<213> ORGANISM: Mus musculus

<400> SEQUENCE: 7
tcagttggtg aggatagcca                                             20

<210> SEQ ID NO 8
<211> LENGTH: 21
<212> TYPE: DNA
<213> ORGANISM: Mus musculus

<400> SEQUENCE: 8
tggtgaggat agccaaggtt c                                           21

<210> SEQ ID NO 9
<211> LENGTH: 19
<212> TYPE: DNA
<213> ORGANISM: Mus musculus

<400> SEQUENCE: 9
aggatagcca aggttctgg                                              19

<210> SEQ ID NO 10
<211> LENGTH: 21
<212> TYPE: DNA
<213> ORGANISM: Mus musculus

<400> SEQUENCE: 10
aacgatatct gggcagaca c                                            21

<210> SEQ ID NO 11
<211> LENGTH: 21
<212> TYPE: DNA
<213> ORGANISM: Mus musculus

<400> SEQUENCE: 11
gatatcttgg gcagacactc c                                           21

<210> SEQ ID NO 12
<211> LENGTH: 21
<212> TYPE: DNA
<213> ORGANISM: Mus musculus

<400> SEQUENCE: 12
aaaaccagca tcttgtcagc c                                           21
```

```
<210> SEQ ID NO 13
<211> LENGTH: 21
<212> TYPE: DNA
<213> ORGANISM: Mus musculus

<400> SEQUENCE: 13
aaccagcatc ttgtcagccc t                                              21

<210> SEQ ID NO 14
<211> LENGTH: 21
<212> TYPE: DNA
<213> ORGANISM: Homo sapiens

<400> SEQUENCE: 14
aacagtctga ggagccgcga g                                              21

<210> SEQ ID NO 15
<211> LENGTH: 21
<212> TYPE: DNA
<213> ORGANISM: Homo sapiens

<400> SEQUENCE: 15
aaaacttggt cggggcaagt a                                              21

<210> SEQ ID NO 16
<211> LENGTH: 21
<212> TYPE: DNA
<213> ORGANISM: Homo sapiens

<400> SEQUENCE: 16
aaaggaccct gtgtcaaaga c                                              21

<210> SEQ ID NO 17
<211> LENGTH: 21
<212> TYPE: DNA
<213> ORGANISM: Homo sapiens

<400> SEQUENCE: 17
aagcaactct accagatcct g                                              21

<210> SEQ ID NO 18
<211> LENGTH: 21
<212> TYPE: DNA
<213> ORGANISM: Homo sapiens

<400> SEQUENCE: 18
aaagctctgg attactgcca c                                              21

<210> SEQ ID NO 19
<211> LENGTH: 21
<212> TYPE: DNA
<213> ORGANISM: Homo sapiens

<400> SEQUENCE: 19
aagggaatca tgcacaggga t                                              21

<210> SEQ ID NO 20
<211> LENGTH: 21
<212> TYPE: DNA
<213> ORGANISM: Homo sapiens

<400> SEQUENCE: 20
aagggaccag agctccttgt g                                              21
```

<210> SEQ ID NO 21
<211> LENGTH: 21
<212> TYPE: DNA
<213> ORGANISM: Homo sapiens

<400> SEQUENCE: 21
aattgccaag gttctgggga c                                               21

<210> SEQ ID NO 22
<211> LENGTH: 21
<212> TYPE: DNA
<213> ORGANISM: Homo sapiens

<400> SEQUENCE: 22
aacattcacg gaagcgctgg g                                               21

<210> SEQ ID NO 23
<211> LENGTH: 21
<212> TYPE: DNA
<213> ORGANISM: Homo sapiens

<400> SEQUENCE: 23
aacaggcacc ttgtcagccc g                                               21

<210> SEQ ID NO 24
<211> LENGTH: 21
<212> TYPE: DNA
<213> ORGANISM: Homo sapiens

<400> SEQUENCE: 24
aaagaggcca tggagcaccc a                                               21

<210> SEQ ID NO 25
<211> LENGTH: 21
<212> TYPE: DNA
<213> ORGANISM: Homo sapiens

<400> SEQUENCE: 25
aaggagcagt cccagccttg t                                               21

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

-continued

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41

<211> LENGTH: 21
<212> TYPE: DNA
<213> ORGANISM: Artificial Sequence
<220> FEATURE:
<223> OTHER INFORMATION: sense strand siRNA

<400> SEQUENCE: 41
gcagggccag aguuuacact t                                              21

<210> SEQ ID NO 42
<211> LENGTH: 21
<212> TYPE: DNA
<213> ORGANISM: Artificial Sequence
<220> FEATURE:
<223> OTHER INFORMATION: sense strand siRNA

<400> SEQUENCE: 42
cacacacaga ccccgagagt t                                              21

<210> SEQ ID NO 43
<211> LENGTH: 21
<212> TYPE: DNA
<213> ORGANISM: Artificial Sequence
<220> FEATURE:
<223> OTHER INFORMATION: sense strand siRNA

<400> SEQUENCE: 43
aauacacaca gaccucgagt t                                              21

<210> SEQ ID NO 44
<211> LENGTH: 21
<212> TYPE: DNA
<213> ORGANISM: Artificial Sequence
<220> FEATURE:
<223> OTHER INFORMATION: sense strand siRNA

<400> SEQUENCE: 44
gaccccgaga guacugggat t                                              21

<210> SEQ ID NO 45
<211> LENGTH: 21
<212> TYPE: DNA
<213> ORGANISM: Artificial Sequence
<220> FEATURE:
<223> OTHER INFORMATION: sense strand siRNA

<400> SEQUENCE: 45
uuugagaggu gggcccaact t                                              21

<210> SEQ ID NO 46
<211> LENGTH: 21
<212> TYPE: DNA
<213> ORGANISM: Artificial Sequence
<220> FEATURE:
<223> OTHER INFORMATION: sense strand siRNA

<400> SEQUENCE: 46
uguccgaguu gcuucucgat t                                              21

<210> SEQ ID NO 47
<211> LENGTH: 21
<212> TYPE: DNA
<213> ORGANISM: Artificial Sequence
<220> FEATURE:
<223> OTHER INFORMATION: sense strand siRNA

<400> SEQUENCE: 47
uggagcuugg guuguaugct t                                         21

<210> SEQ ID NO 48
<211> LENGTH: 21
<212> TYPE: DNA
<213> ORGANISM: Artificial Sequence
<220> FEATURE:
<223> OTHER INFORMATION: sense strand siRNA

<400> SEQUENCE: 48
caguugguga ggauagccat t                                         21

<210> SEQ ID NO 49
<211> LENGTH: 21
<212> TYPE: DNA
<213> ORGANISM: Artificial Sequence
<220> FEATURE:
<223> OTHER INFORMATION: sense strand siRNA

<400> SEQUENCE: 49
gugaggauag ccaagguuct t                                         21

<210> SEQ ID NO 50
<211> LENGTH: 21
<212> TYPE: DNA
<213> ORGANISM: Artificial Sequence
<220> FEATURE:
<223> OTHER INFORMATION: sense strand siRNA

<400> SEQUENCE: 50
aggauagcca agguucuggt t                                         21

<210> SEQ ID NO 51
<211> LENGTH: 21
<212> TYPE: DNA
<213> ORGANISM: Artificial Sequence
<220> FEATURE:
<223> OTHER INFORMATION: sense strand siRNA

<400> SEQUENCE: 51
cgauaucuug ggcagacact t                                         21

<210> SEQ ID NO 52
<211> LENGTH: 21
<212> TYPE: DNA
<213> ORGANISM: Artificial Sequence
<220> FEATURE:
<223> OTHER INFORMATION: sense strand siRNA

<400> SEQUENCE: 52
uaucuugggc agacacucct t                                         21

<210> SEQ ID NO 53
<211> LENGTH: 21
<212> TYPE: DNA
<213> ORGANISM: Artificial Sequence
<220> FEATURE:
<223> OTHER INFORMATION: sense strand siRNA

<400> SEQUENCE: 53
aaccagcacc uugucagcct t                                         21

<210> SEQ ID NO 54
<211> LENGTH: 21
<212> TYPE: DNA

```
<213> ORGANISM: Artificial Sequence
<220> FEATURE:
<223> OTHER INFORMATION: sense strand siRNA

<400> SEQUENCE: 54
ccagcaccuu gucagcccut t                                              21

<210> SEQ ID NO 55
<211> LENGTH: 21
<212> TYPE: DNA
<213> ORGANISM: Artificial Sequence
<220> FEATURE:
<223> OTHER INFORMATION: sense strand siRNA

<400> SEQUENCE: 55
cagccugagg agccgcgagt t                                              21

<210> SEQ ID NO 56
<211> LENGTH: 21
<212> TYPE: DNA
<213> ORGANISM: Artificial Sequence
<220> FEATURE:
<223> OTHER INFORMATION: sense strand siRNA

<400> SEQUENCE: 56
aacuuggucg gggcaaguat t                                              21

<210> SEQ ID NO 57
<211> LENGTH: 21
<212> TYPE: DNA
<213> ORGANISM: Artificial Sequence
<220> FEATURE:
<223> OTHER INFORMATION: sense strand siRNA

<400> SEQUENCE: 57
aggacccugu gucaaagact t                                              21

<210> SEQ ID NO 58
<211> LENGTH: 21
<212> TYPE: DNA
<213> ORGANISM: Artificial Sequence
<220> FEATURE:
<223> OTHER INFORMATION: sense strand siRNA

<400> SEQUENCE: 58
gcaacucuac cagauccugt t                                              21

<210> SEQ ID NO 59
<211> LENGTH: 21
<212> TYPE: DNA
<213> ORGANISM: Artificial Sequence
<220> FEATURE:
<223> OTHER INFORMATION: sense strand siRNA

<400> SEQUENCE: 59
agcucuggau uacugccact t                                              21

<210> SEQ ID NO 60
<211> LENGTH: 21
<212> TYPE: DNA
<213> ORGANISM: Artificial Sequence
<220> FEATURE:
<223> OTHER INFORMATION: sense strand siRNA

<400> SEQUENCE: 60
gggaaucaug cacagggaut t                                              21
```

```
<210> SEQ ID NO 61
<211> LENGTH: 21
<212> TYPE: DNA
<213> ORGANISM: Artificial Sequence
<220> FEATURE:
<223> OTHER INFORMATION: sense strand siRNA

<400> SEQUENCE: 61
gggaccagag cuccuugugt t                                               21

<210> SEQ ID NO 62
<211> LENGTH: 21
<212> TYPE: DNA
<213> ORGANISM: Artificial Sequence
<220> FEATURE:
<223> OTHER INFORMATION: sense strand siRNA

<400> SEQUENCE: 62
uugccaaggu ucugggract t                                               21

<210> SEQ ID NO 63
<211> LENGTH: 21
<212> TYPE: DNA
<213> ORGANISM: Artificial Sequence
<220> FEATURE:
<223> OTHER INFORMATION: sense strand siRNA

<400> SEQUENCE: 63
cauucacgga agcgcugggt t                                               21

<210> SEQ ID NO 64
<211> LENGTH: 21
<212> TYPE: DNA
<213> ORGANISM: Artificial Sequence
<220> FEATURE:
<223> OTHER INFORMATION: sense strand siRNA

<400> SEQUENCE: 64
caggcaccuu gucagcccgt t                                               21

<210> SEQ ID NO 65
<211> LENGTH: 21
<212> TYPE: DNA
<213> ORGANISM: Artificial Sequence
<220> FEATURE:
<223> OTHER INFORMATION: sense strand siRNA

<400> SEQUENCE: 65
agaggccaug gagcacccat t                                               21

<210> SEQ ID NO 66
<211> LENGTH: 21
<212> TYPE: DNA
<213> ORGANISM: Artificial Sequence
<220> FEATURE:
<223> OTHER INFORMATION: sense strand siRNA

<400> SEQUENCE: 66
ggagcagucc cagccuugut t                                               21

<210> SEQ ID NO 67

<400> SEQUENCE: 67

000
```

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79
<400> SEQUENCE: 79

000

<210> SEQ ID NO 80
<400> SEQUENCE: 80

000

<210> SEQ ID NO 81
<400> SEQUENCE: 81

000

<210> SEQ ID NO 82
<400> SEQUENCE: 82

000

<210> SEQ ID NO 83
<400> SEQUENCE: 83

000

<210> SEQ ID NO 84
<400> SEQUENCE: 84

000

<210> SEQ ID NO 85
<400> SEQUENCE: 85

000

<210> SEQ ID NO 86
<400> SEQUENCE: 86

000

<210> SEQ ID NO 87
<211> LENGTH: 19
<212> TYPE: DNA
<213> ORGANISM: Artificial Sequence
<220> FEATURE:
<223> OTHER INFORMATION: sh-CK2alpha

<400> SEQUENCE: 87
caattgtacc agacgttaa                    19

<210> SEQ ID NO 88
<211> LENGTH: 21
<212> TYPE: DNA
<213> ORGANISM: Artificial Sequence
<220> FEATURE:
<223> OTHER INFORMATION: sh-ATM

<400> SEQUENCE: 88
tgatggtctt aaggaacatc t                 21